United States Patent [19]

Hutchison

[11] Patent Number: 4,604,397
[45] Date of Patent: Aug. 5, 1986

[54] CERTAIN BENZO-(PYRANO AND THIOPYRANO)-PYRIDINES, USEFUL AS CNS AGENTS

[75] Inventor: Alan J. Hutchison, Verona, N.J.

[73] Assignee: Ciba-Geigy Corporation, Ardsley, N.Y.

[21] Appl. No.: 771,934

[22] Filed: Sep. 3, 1985

Related U.S. Application Data

[63] Continuation-in-part of Ser. No. 609,037, May 10, 1984, abandoned.

[30] Foreign Application Priority Data

May 6, 1985 [EP] European Pat. Off. ........ 85810208.0

[51] Int. Cl.$^4$ .................. A61K 31/38; A61K 31/395; C07D 491/02; C07D 471/02
[52] U.S. Cl. ...................................... 514/291; 546/65; 546/80; 546/89
[58] Field of Search ........................... 546/89, 80, 65; 514/291

[56] References Cited

U.S. PATENT DOCUMENTS

| | | | |
|---|---|---|---|
| 3,689,497 | 9/1972 | Brown | 546/89 |
| 3,915,996 | 10/1975 | Wright et al. | 260/345 |
| 4,025,630 | 5/1977 | Dren et al. | 424/256 |
| 4,198,511 | 4/1980 | Connor | 546/89 |
| 4,210,758 | 7/1980 | Connor | 546/89 |
| 4,292,316 | 9/1981 | Dren et al. | 424/248.56 |
| 4,385,056 | 5/1983 | Loosen | 546/89 |
| 4,420,480 | 12/1983 | Jones | 546/89 |
| 4,540,691 | 9/1985 | Horn | 546/89 |

FOREIGN PATENT DOCUMENTS

| | | | |
|---|---|---|---|
| 0046903 | 3/1982 | Japan | 546/89 |
| 751674 | 3/1976 | South Africa | 546/89 |

OTHER PUBLICATIONS

J. Med. Chem. 25 925/(1982).

Abstract European Patent 99 303.

Primary Examiner—Henry H. Jiles
Assistant Examiner—J. Richter
Attorney, Agent, or Firm—Norbert Gruenfeld

[57] ABSTRACT

Disclosed are the compounds of formula I

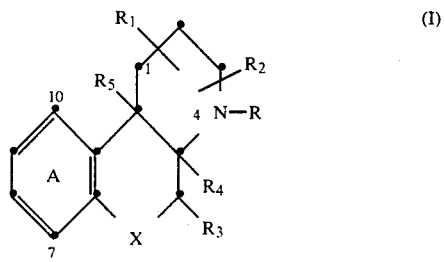

wherein X represents oxygen or sulfur; ring A is unsubstituted or substituted by one to three identical or different substituents selected from hydroxy, hydroxy-lower alkyl, etherified hydroxy, etherified hydroxy-lower alkyl, acyloxy, acyloxy-lower alkyl, halogen, lower alkyl, trifluoromethyl, amino, mono- and di-lower alkylamino and acylamino; or ring A is substituted by one lower alkylenedioxy; R represents hydrogen, lower alkyl or aryl-lower alkyl; $R_1$ represents hydrogen, lower alkyl, lower alkylthio-lower alkyl, amino, acylamino, (amino, mono- or di-lower alkylamino)-lower alkyl, carboxy, lower alkoxycarbonyl, carbamoyl or mono- or di-lower alkylcarbamoyl; $R_2$ to $R_5$ represent hydrogen or lower alkyl; the dehydro derivatives thereof with a double bond at the 1,2-position, or at the 1,10b-position in which case $R_5$ is absent; or a pharmaceutically acceptable salt thereof; methods for their synthesis; pharmaceutical compositions thereof; and use thereof as psychactive agents for the treatment of central nervous system disorders.

28 Claims, No Drawings

CERTAIN BENZO-(PYRANO AND THIOPYRANO)-PYRIDINES, USEFUL AS CNS AGENTS

CROSS-REFERENCE TO RELATED APPLICATION

This application is a continuation-in-part of Application Ser. No. 609,037 filed May 10, 1984 now abandoned.

SUMMARY OF THE INVENTION

The present invention is concerned with tetrahydro and hexahydro 4H-[1]-benzopyrano- and benzothiopyrano-[3,4-b]pyridines active as psychotropic receptor modulators and useful as psychoactive agents for the treatment of central nervous system disorders, processes for preparing same, pharmaceutical compositions comprising said compounds, and methods of treating syndromes, conditions and diseases in mammals responsive to the effect of such a psychotropic receptor modulator by administration of said compounds or a pharmaceutical composition comprising said compounds.

DETAILED DESCRIPTION OF THE INVENTION

Particularly the invention is concerned with the novel 4H-[1]-benzopyrano[3,4-b]pyridine and 4H-[1]-benzothiopyrano[3,4-b]pyridine derivatives of formula I

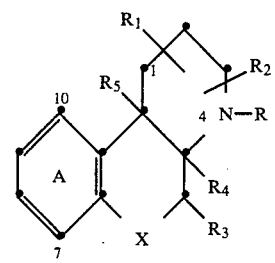

wherein X represents oxygen or sulfur; ring A is unsubstituted or substituted by one to three identical or different substituents selected from hydroxy, hydroxy-lower alkyl, etherified hydroxy, etherified hydroxy-lower alkyl, acyloxy, acyloxy-lower alkyl, halogen, lower alkyl, trifluoromethyl, amino, mono- and di-lower alkylamino and acylamino; or ring A is substituted by one lower alkylenedioxy; R represents hydrogen, lower alkyl or aryl-lower alkyl; $R_1$ represents hydrogen, lower alkyl, lower alkylthio-lower alkyl, amino, acylamino, (amino, mono- or di-lower alkylamino)-lower alkyl, carboxy, lower alkoxycarbonyl, carbamoyl or mono- or di-lower alkylcarbamoyl; $R_2$ to $R_5$ represent hydrogen or lower alkyl; the dehydro derivatives thereof with a double bond at the 1,2-position, or at the 1,10b-position in which case $R_5$ is absent; and pharmaceutically acceptable salts thereof.

The 1,10b- and 1,2-dehydro derivatives of the compounds of formula I are represented by formula Ia and Ib respectively

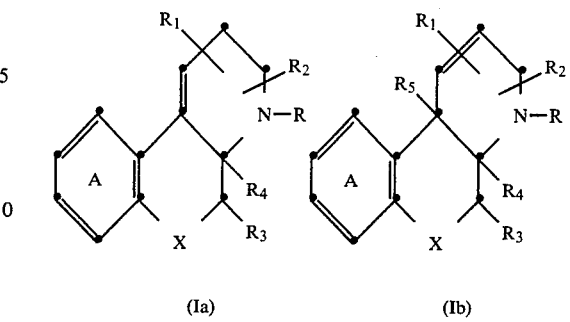

wherein ring A, R and $R_1$ to $R_5$ are as defined above.

One particular embodiment of the invention is represented by the compounds of the formula I, formula Ia and Ib and salts wherein X represents oxygen.

Another embodiment of the invention is represented by compounds of the formula I, Ia and Ib and salts wherein X represents sulfur.

Preferred are the compounds of formula I, Ia and Ib wherein X represents oxygen or sulfur; ring A is unsubstituted or substituted by one to three substituents selected from hydroxy, acyloxy, etherified hydroxy, hydroxymethyl, lower alkyl, acyloxymethyl, etherified hydroxymethyl, halogen and trifluoromethyl; or ring A is substituted by one lower alkylenedioxy; R, $R_1$ to $R_5$ represent hydrogen or lower alkyl; and pharmaceutically acceptable salts thereof.

Further preferred are the compounds of formula II

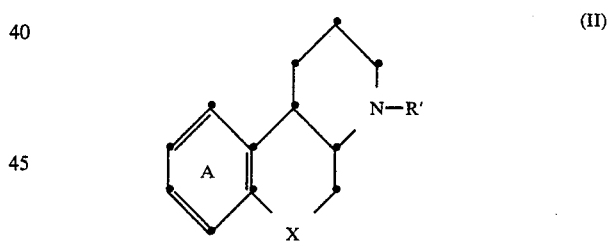

wherein ring A is unsubstituted or substituted by one to three identical or different substituents selected from hydroxy, hydroxymethyl, acyloxy, acyloxymethyl, lower alkyl, lower alkoxy and halogen; X represents oxygen or sulfur; R' represents lower alkyl; the 1,10b-dehydro derivatives thereof; and pharmaceutically acceptable salts thereof.

Particularly preferred are compounds of formula II wherein X represents oxygen; ring A is monosubstituted by hydroxy, lower alkanoyloxy, benzoyloxy or pyridylcarbonyloxy; R' represents lower alkyl of 1 to 4 carbon atoms and the pharmaceutically acceptable salts thereof.

Another preferred embodiment of the invention relates to the compounds of formula III

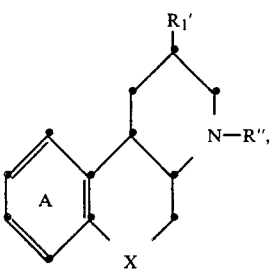

(III)

wherein ring A is unsubstituted or substituted by one to three identical or different substituents selected from hydroxy, hydroxymethyl, acyloxy, acyloxymethyl, lower alkoxy and halogen; X represents oxygen or sulfur; R'' represents lower alkyl; $R_1'$ represents lower alkylthio-lower alkyl, acylamino, (amino, mono- or di-lower alkylamino)-lower alkyl, carboxy, lower alkoxycarbonyl, carbamoyl, mono- or di-lower alkylcarbamoyl; and pharmaceutically acceptable salts thereof.

The above compounds of formulae I, Ib, II or III may be in the form of cis or trans ring fused compounds. Depending on the nature of $R_1$ ($R_1'$) to $R_5$ and the resulting number of asymmetric carbon atoms, the compounds of formulae I, II or III also exist in form of a number of racemates and optical antipodes thereof. Thus the compounds of the invention exist in the form of stereoisomers, e.g. geometric isomers, racemates, pure enantiomers or mixtures thereof, all of which are within the scope of the invention.

Preferred are the compounds of formulae I, II or III which have a trans 4a,10b-ring junction.

The general definitions used herein have the following meaning within the scope of the present invention.

The term "lower" referred to above and hereinafter in connection with organic radical or compounds respectively defines such with up to and including 7, preferably up to and including 4 and advantageously one or two carbon atoms.

A lower alkyl group preferably contains 1 to 4 carbon atoms and represents for example ethyl, propyl, butyl or advantageously methyl.

A lower alkoxy group preferably contains 1 to 4 carbon atoms and represents for example ethoxy, propoxy or advantageously methoxy.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Acyl in acyloxy, acyloxy-lower alkyl, acylamino represents preferably lower alkanoyl, aroyl, lower alkoxycarbonyl, carbamoyl or mono- or di-lower alkylcarbamoyl.

Lower alkanoyl is preferably acetyl, propionyl or butyryl.

Aroyl is preferably benzoyl or benzenesulfonyl; benzoyl or benzenesulfonyl substituted by one to three of lower alkyl, lower alkoxy, halogen or trifluoromethyl; or heteroaroyl, e.g. thienoyl, pyrroloyl, 2-, 3- or 4-pyridylcarbonyl advantageously nicotinoyl.

Aryl as in aryl-lower alkyl is preferably phenyl or phenyl substituted by one to three lower alkyl, lower alkoxy, halogen or trifluoromethyl; and aryl-lower alkyl is advantageously benzyl or phenethyl optionally substituted by one to three lower alkyl, lower alkoxy, halogen or trifluoromethyl.

Lower alkanoyloxy is preferably acetoxy or propionyloxy; lower alkanoylamino is preferably acetamido or propionamido; aroyloxy is preferably benzenesulfonyloxy, benzoyloxy, benzoyloxy or benzenesulfonyloxy substituted on the benzene ring by one to three of lower alkyl, lower alkoxy, halogen or trifluoromethyl, or heteroaroyloxy.

Heteroaroyloxy is preferably 2-, 3- or 4-pyridylcarbonyloxy, advantageously nicotinoyloxy.

Lower alkanoyloxy-lower alkyl is preferably lower alkanoyloxymethyl.

Aroyloxy-lower alkyl is preferably aroyloxymethyl.

Lower alkoxycarbonyl is preferably ethoxycarbonyl or methoxycarbonyl.

Halogen is preferably fluoro or chloro, but may also be bromo or iodo.

Lower alkylenedioxy represents preferably ethylenedioxy or methylenedioxy.

Hydroxy-lower alkyl is preferably hydroxymethyl, hydroxyethyl or hydroxypropyl, advantageously hydroxymethyl.

Etherified hydroxy represents preferably lower alkoxy, e.g. methoxy or ethoxy; lower alkenyloxy, e.g. allyloxy; lower alkynyloxy, e.g. propargyloxy;($C_{3-6}$)-cycloalkyl-lower alkoxy, e.g. cyclopropylmethoxy; benzyloxy unsubstituted or substituted on the phenyl ring e.g. by lower alkyl, halogen or lower alkoxy, such as methyl, chloro or methoxy respectively; or pyridyl-lower alkoxy, e.g. pyridylmethoxy.

Acylamino represents lower alkanoylamino, aroylamino, heteroaroylamino, lower alkoxycarbonylamino, carbamoylamino or mono- or di-lower alkylcarbamoylamino, wherein the respective groups have the meaning as defined above.

Acyloxy represents lower alkanoyloxy, aroyloxy, heteroaroyloxy, lower alkoxycarbonyloxy, carbamoyloxy, or mono- or di-lower alkylcarbamoyloxy wherein the respective groups have the meaning as defined above.

Mono- or di-lower alkylamino is preferably mono- or di-(methyl, ethyl, propyl)-amino.

Mono- or di-lower alkylcarbamoyl is preferably mono- or di-N-(methyl, ethyl, propyl)-carbamoyl.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

In addition to the pharmaceutically acceptable salts cited above, any prodrug derivatives, e.g., pharmaceutically acceptable esters of phenols or alcohols (compounds of formula I, II, III and dehydro derivatives wherein ring A is substituted by hydroxy or hydroxy-lower alkyl) of this invention that may be convertible by solvolysis or under physiological conditions to said phenols or alcohols, represent a further object of this invention.

Such prodrug esters are preferably as defined above straight chain or branched lower alkanoyl esters, e.g., the acetyl, isobutyryl, pivaloyl ester; aroyl esters, e.g., the benzoyl, nicotinoyl ester; carbamoyl esters (carbamates), e.g. the mono- or di-ethylcarbamoyl or N-mono- or di-methylcarbamoyl ester.

The novel compounds of the invention are active in state of art in vitro and in vivo test systems which have been correlated with effectiveness for the treatment of central nervous system disorders in mammals including man. Selective presynaptic dopamine receptor agonists and $\alpha_2$-adrenergic receptor agonists can be used e.g. for the treatment of dyskinesia, parkinsonism or psychotic conditions such as schizophrenia; serotonin receptor agonists and $\alpha_2$-receptor antagonists can be used e.g. for the treatment of depression, cognition deficiencies and minimal brain dysfunctions.

Thus the compounds of this invention possess valuable pharmalogical properties in mammals, primarily central nervous system modulating or psychopharmacological properties, e.g. primarily neuroleptic and/or antidepressant effects by inter alia modulating presynaptic dopamine receptors, and/or presynaptic $\alpha_2$-adrenergic receptors and/or serotonin receptors in the brain. For instance their selective presynaptic dopamine receptor stimulating (agonistic) properties are indicative of e.g. neuroleptic (antipsychotic) activity, their serotonin receptor stimulating (agonistic) properties and $\alpha_2$-adrenergic receptor blocking (antagonistic) properties are indicative of e.g. antidepressant activity.

The above cited properties are demonstrable in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-4}$ molar and $10^{-9}$ molar concentrations. The dosage in vivo may range between about 0.01 and 50 mg/kg/day, preferably between about 0.05 and 30 mg/kg/day, advantageously between about 0.1 and 20 mg/kg/day.

The presynaptic dopamine receptor binding properties indicative of the presynaptic dopamine receptor regulatory, e.g. agonistic activity, of the compounds of the invention are determined in the dopamine binding assay in vitro by the following method involving the displacement of the dopamine agonist 2-amino-6,7-dihydroxy-1,2,3,4-tetrahydronaphthalene ($^3$H-ADTN) from membranes from calf-caudate nucleus. [Eur. J. Pharmacol. 55, 137 (1979)].

Bovine brain tissue is homogenized in 50 volumes (based on original tissue weight) of 50 mM Tris-HCl buffer, pH 7.7 at 25° C., using a Brinkman Polytron, setting 6 for 20 seconds. The homogenate is centrifuged at 50,000×g for 10 minutes. The pellet is resuspended in 50 volumes of 50 mM Tris-HCl buffer, pH 7.7 and recentrifuged. The final pellet is resuspended in 200 volumes of incubation media containing: 50 mM Tris-HCl buffer, pH 7.7; 0.1% ascorbic acid; 0.001 mM pargyline; 120 mM NaCl; 5 mM KCl, 2 mM CaCl$_2$ and 1 mM MgCl$_2$.

In the binding assay, triplicate 2 ml samples (equivalent to 5 mg/ml original tissue) of the membrane suspension are incubated for 60 minutes at 25° C. with 0.2 nM $^3$H-ADTN without or in the presence of various concentrations of test compound in solvent. The reaction is terminated by filtering with 5 ml of cold 50 mM Tris-HCl buffer pH 7.7. The filters are placed in scintillation vials with 5 ml of scintillation solution, disrupted by vigorous mechanical shaking for 90 minutes, and counted for radioactivity.

The IC$_{50}$ values represent the concentration of test compounds required to inhibit the specific binding of 0.2 nM $^3$H-ADTN by 50%, and are determined graphically.

Indicative of potential neuroleptic activity of the compounds of the invention, the in-vivo presynaptic dopamine agonist activity (also called dopamine autoreceptor agonist activity) is determined in the rat gamma-butyrolactone (GBL) model by a modification of the procedure described by Walters and Roth, Naunyn Schmiedeberg's Arch. Pharmacol. 296, 5 (1976). In this model, a presynaptic dopamine agonist inhibits the GBL-induced accumulation of the dopamine precursor DOPA after pretreatment with 3-hydroxybenzylhydrazine (NSD-1015), a DOPA decarboxylase inhibitor.

Test compounds are dissolved in 0.9% saline, with sodium metabisulfite to prevent oxidation, if required. Animals are treated with i.p. injections of test compounds or saline, followed by $\gamma$-butyrolactone (GBL, 750 mg/kg i.p.) or saline for control animals 15 minutes later, and finally with NSD-1015 (100 mg/kg i.p.) 5 minutes after the administration of GBL. Thirty minutes after the administration of NSD-1015, animals are sacrificed, brains are removed, and striate are isolated, then frozen at −70° C. until deproteinization, extraction and analysis. Using micropipette columns packed with activated alumina, DOPA (dihydroxyphenylamine) and other catecholamines are extracted with striatal tissue deproteininized with 0.4M perchloric acid. Dihydroxyphenylalanine (DOPA) is analyzed by High Pressure Liquid Chromatography/Electrochemistry (HPLC/EC) techniques using a Bio-analytical Systems (BAS) Model LC-150 series Liquid Chromatograph. Catechols are eluted from a 5 micron (250×4.6 cm) ODS reverse phase column (BAS) with a 0.1M NaH$_2$PO$_4$ buffer containing 0.3 mM heptanesulfonic acid-sodium salt and 0.1 mM Na$_2$EDTA. Compounds are detected with an electro-chemical detector having an oxidizing potential of 0.7 volts and sensitivity setting of 20 nAmps/V. Tissue concentrations and recoveries are calculated by using the internal standard dihydroxybenzylamine (DHBA). Recoveries range from 60–90%. Data is statistically analysed by one-way Analysis of Variance with Duncan's Multiple Comparison Test. The activity of the test compounds is determined as the percent inhibition of DOPA accumulation at a given dose. ED$_{50}$ (dose at which the DOPA accumulation is inhibited by 50%) values are determined by plotting the percent inhibition of DOPA accumulation versus log$_{10}$ of the dose of test compound administered. The same method is also applicable to oral administration of the test compounds.

The selectivity of the compounds of the invention as to pre-synaptic dopamine agonist activity is determined in vitro by binding studies in displacing $^3$H-spiroperidol from post-synaptic dopamine receptors. Weak binding in this assay is indicative of selectivity.

In vivo such selectivity can be determined by measurement of the degree of reversal of reserpine induced hypomotility in the rat. The relative absence of such reversal at effective doses (e.g. in the GBL model) is indicative of selective presynaptic dopamine agonist activity.

Illustrative of the invention, trans-4-propyl-9-hydroxy-1,2,3,4a,5,10b-hexahydro-4H-[1]-benzopyrano[3,4-b]-pyridine hydrochloride has an $IC_{50}$ of about $3\times10^{-8}M$ in the $^3$H-ADTN presynaptic dopamine receptor assay.

Also illustrative of the invention, trans-4-propyl-9-hydroxy-1,2,3,4a,5,10b-hexahydro-4H-[1]-benzopyrano-[3,4-b]pyridine hydrochloride displays an $ED_{50}$ of about 0.16 mg/kg i.p. in the GBL model in the rat whereas the $ED_{50}$ in the rat for reversal of reserpine-induced hypomotility is about 10 mg/kg i.p. Said compound is also active in the GBL model orally at a dose of about 0.5 mg/kg.

Further illustrative of the invention, 4-propyl-9-hydroxy-2,3,4a,5-tetrahydro-4H-[1]-benzothiopyrano[3,4-b]-pyridine hydrochloride has an $IC_{50}$ of about $1\times10^{-8}M$, trans-4-propyl-7-hydroxy-1,2,3,4a,5,10b-hexahydro-4H-[1]-benzopyran[3,4-b]-pyridine hydrochloride has an $IC_{50}$ of about $6\times10^{-8}M$, and trans-4-butyl-7-hydroxy-1,2,3,4a,5,10b-hexahydro-4H-[1]-benzopyran-[3,4-b]pyridine hydrochloride has an $IC_{50}$ of about $2\times10^{-8}M$ in the $^3$H-ADTN presynaptic dopamine binding assay [Bennett and Synder, Mol. Pharmacol. 12, 273 (1976)] as follows:

The serotonin binding properties indicative of serotonin agonistic receptor regulating activity of compounds of the invention are determined in the in vitro binding assay as follows:

Membrane suspensions are prepared from calf brain and incubated with $^3$H-serotonin by a modification of the procedure described by Bennett and Snyder. Caudate nuclei are dissected from freshly obtained calf brains; they are frozen and stored at $-70°$ C. for up to 3 months. For each binding experiment, a portion of tissue is homogenized with a Brinkmann Polytron in 50 volumes (w/v) of ice-cold 50 mM Tris-HCl (pH 7.7 at 25° C.) containing 10 mM dithiothreitol. The homogenate is centrifuged twice at $50,000\times g$ for 10 minutes with rehomogenization of the pellet in fresh buffer between spins. The final pellet is homogenized in 100 volumes (based on original tissue weight) cold 50 mM Tris-HCl (pH 7.6 at 25° C.) containing 10M pargyline, 0.1% ascorbic acid, 120 mM NaCl, 5 mM KCl, 2 mM $CaCl_2$, 1 mM $MgCl_2$ and 10 mM dithiothreitol. The suspension is warmed in a 37° C. bath for 10 minutes and then returned to ice.

In the binding assay, 2-ml aliquots of the final tissue suspension (equivalent to 20 mg of original wet tissue) are added to tubes (on ice) containing $^3$H-serotonin with or without test compound freshly dissolved in 0.1% ascorbic acid. The final concentration of $^3$H-serotonin is 7 nM. Test compounds are present over a wide range of concentrations, with triplicate tubes for each concentration. Tubes are incubated at 37° C. for 10 minutes and the suspensions are immediately filtered under vacuum through Whatman GF/B glass fiber filters. The filters are washed with 10 ml of cold Tris-HCl (pH 7.7 at 25° C.), placed in scintillation vials with 12 ml of scintillation solution, disrupted by vigorous mechanical shaking for 90 minutes and counted for radioactivity. The $IC_{50}$ values (concentrations of test compounds required to inhibit the specific binding of 7 nM $^3$H-serotonin by 50%) are determined graphically.

Illustrative of the invention, trans 4-methyl-7-methoxy-1,2,3,4a,5,10b-hexahydro-4H-[1]-benzopyrano[3,4-b]pyridine hydrochloride has an $Ic_{50}$ of about $8\times10^{-8}M$, trans 4-methyl-10-hydroxy-1,2,3,4a,5,10b-hexahydro-4H-[1]-benzopyrano[3,4-b]pyridine hydrochloride has an $IC_{50}$ of about $4\times10^{-7}M$, trans 8-bromo-7-methoxy-4-methyl-1,2,3,4a,5,10b-hexahydro-4H-[1]-benzopyrano[3,4-b]pyridine hydrochloride and trans-10-methoxy-4-propyl-1,2,3,4a,5,10b-hexahydro-4H-[1]-benzopyrano[3,4-b]pyridine hydrochloride have an $IC_{50}$ of about $2\times10^{-8}M$, in the $^3$H-serotonin binding assay.

The serotonin receptor agonist activity is determined in vivo by measuring the decrease in the accumulation of 5-hydroxytryptophane in the brain after administration of a test compound in the rat, as described in J. Med. Chem. 21, 864 (1978).

Illustrative of the invention, trans 8-bromo-7-methoxy-4-methyl-1,2,3,4a,5,10b-hexahydro-4H-[1]-benzopyrano[3,4-b]pyridine hydrochloride decreases the accumulation of 5-hydroxytryptophane in the frontoparietal cortex of rat brain by about 25% when administered at a dose of 2.5 mg/kg s.c. Trans-7-hydroxy-4,8-dimethyl-1,2,3,4a,5,10b-hexahydro-4H-[1]-benzopyrano[3,4-b]pyridine hydrochloride is similarly effective at a dose of 0.1 mg/Kg.

The aforesaid advantageous properties render the compounds of the invention useful as therapeutic agents with psychotropic properties. They exhibit selective central nervous system modulating activity and as such are useful in mammals, especially as psychoactive agents and, depending on their specific effects on central nervous system receptors, e.g. an neuroleptic (antipsychotic) agents for the treatment of psychotic conditions (schizophrenia), as psychostimulants for the treatment of depression, cognition deficiencies (senile dementia) and minimal brain disfunction; as anxiolytics for the treatment of anxiety; and as appetite suppressants for the treatment of obesity.

Most useful as selective presynaptic dopamine receptor agonists for the treatment of psychotic conditions are the compounds of the invention represented by formula II, particularly the trans ring-fused isomers thereof, or the 1,10b-dehydro derivatives thereof, wherein X is oxygen or sulfur; R' is alkyl of 3 to 5 carbon atoms; ring A is monosubstituted at the 7-, 8- or 9-position by hydroxy, acyloxy, hydroxymethyl or acyloxymethyl; or ring A is disubstituted at two of the 7-, 8- or 9-positions by one of the groups chosen from hydroxy and acyloxy and the other group chosen from hydroxy, acyloxy and halogen; and the pharmaceutically acceptable salts thereof.

Preferred as selective presynaptic dopamine receptor agonists are the compounds of formula II, particularly the trans ring-fused isomers, wherein X is oxygen; R' is straight chain alkyl of 3 to 5 carbon atoms; ring A is monosubstituted at the 7-, 8- or 9-position by hydroxy, lower alkanoyloxy, aroyloxy, hydroxymethyl, lower alkanoyloxymethyl or aroyloxymethyl; and pharmaceutically acceptable salts thereof.

Most preferred as selective presynaptic dopamine receptor agonists are the compounds of formula II, particularly the trans ring-fused isomers, wherein X is oxygen; ring A is monosubstituted at the 7- or 9-position by hydroxy, lower alkanoyloxy, benzoyloxy or nicotinoyloxy; R' is n-propyl or n-butyl; and the pharmaceutically acceptable salts thereof.

Preferred as selective serotonin receptor agonists are the compounds of formula II, particularly the trans ring-fused isomers, wherein X is oxygen; R' is methyl, ethyl or n-propyl; ring A is monosubstituted particularly at the 7- or 10-position by hydroxy, lower alkoxy, lower alkanoyloxy, benzoyloxy or nicotinoyloxy; or ring A is disubstituted, particularly at the 7- and 8-, 7- and 10-, or 8- and 10-positions by one group chosen from hydroxy and lower alkoxy and the other group chosen from lower alkyl and halogen; and the pharmaceutically acceptable salts thereof. Most preferred are said compounds wherein ring A is mono-substituted at the 10-position by hydroxy or lower alkoxy; or ring A is di-substituted at the 7-position by hydroxy or lower alkoxy and at the 8-position by lower alkyl or halogen.

The compounds of the invention, i.e. compounds of formula I hereinabove, the 1,2 or 1,10b-dehydro derivatives thereof of formula Ia and Ib, are prepared using conventional chemical methodology applied to processes which comprise:

(a) reducing a compound of the formula IV

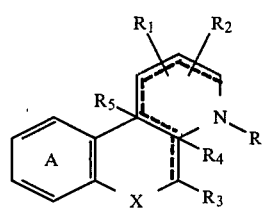

wherein dotted lines represent positions of double bonds, the optional substituents on ring A, X, R, and $R_1-R_5$ are as defined above provided that $R_4$ and $R_5$ are only present if carbon atoms to which they are attached are not part of a double bond; with a suitable reducing agent to saturate one or more double bonds; or (b) reducing a compound of formula V

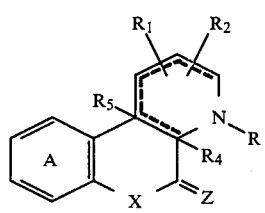

wherein dotted lines represent positions of optional double bonds, X, R, $R_1-R_5$ and optional substituents on ring A have meaning as defined hereinabove; and Z is oxo; with a suitable reducing agent; or (c) reducing a compound of formula VI

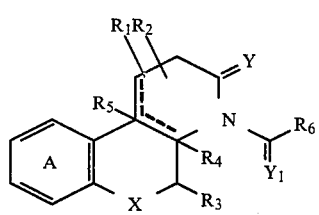

wherein dotted lines represent positions of optional double bonds, X, R, $R_1-R_5$ and optional substituents on ring A have meaning as defined hereinabove; $R_6$ represents hydrogen, aryl, lower alkyl or aryl-lower alkyl in which lower alkyl represents alkyl with up to 6 carbon atoms; Y and $Y_1$ represent oxo, or one of Y and $Y_1$ represents oxo and the other represents two hydrogens; with an appropriate reducing agent; or (d) reducing the pyridinium ring in a quaternary salt of the formula VII

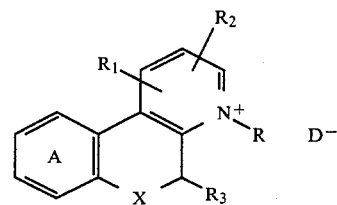

wherein X, R, $R_1-R_3$ and the optional substituents on ring A have meaning as defined hereinabove, and $D^-$ is the anion of an organic or inorganic acid; or (e) reacting a compound of the formula VIII

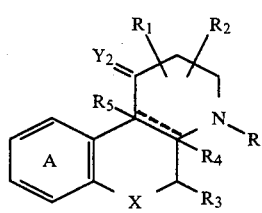

wherein dotted line represents the position of an optional double bond; X, R, $R_1-R_5$ and optional substituents on ring A have meaning as defined hereinabove; and $Y_2$ is oxo or oxo protected in form of a thioketal; or $Y_2$ represents one hydroxy, esterified or etherified hydroxy, and one hydrogen; by treatment with a suitable reducing agent and/or elimination reagent; or (f) reducing a compound of the formula IX

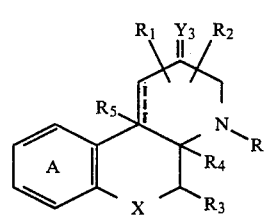

wherein the dotted line represents the position of an optional double bond; X, R, $R_1-R_5$ and optional substituents on ring A have meaning as defined hereinabove; and $Y_3$ is oxo or oxo protected in the form of a thioketal; with an effective reducing agent; or (g) cyclizing a compound of the formula X

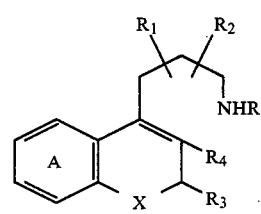

wherein X, R, $R_1-R_4$ and optional substituents on ring A have meaning as defined hereinabove to a compound of formula Ia; and optionally reducing the double bond in the resulting product to obtain a compound of formula I; or (h) cyclizing a compound of formula XI

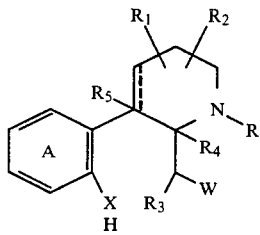

wherein X, R, $R_1$–$R_5$ and optional substituents on ring A have meaning as defined hereinabove; the dotted lines represent the position of an optional double bond and W represents reactive esterified hydroxy; or (i) cyclizing a compound of the formula XII

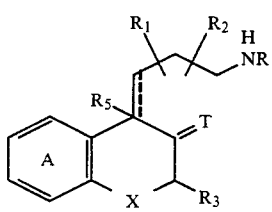

wherein the dotted lines represent the position of an optional double bond; X, R, $R_1$–$R_3$ and $R_5$, and optional substituents on ring A have meaning as defined hereinabove; T is oxo or T represents reactive esterified hydroxy together with hydrogen or lower alkyl; and if required reducing the resulting product; or (j) cyclizing a compound of formula XIII

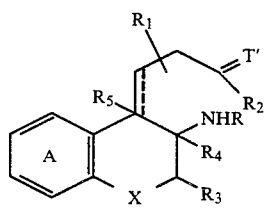

wherein the dotted lines represent the position of an optional double bond; X, R, $R_1$–$R_5$ and optional substituents on ring A have meaning as defined hereinabove; and T' represents oxo or T' represents reactive esterified hydroxy together with hydrogen; and, if required, reducing the resulting product; or (k) cyclizing a compound of the formula XIV

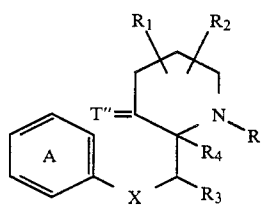

wherein X, R, $R_1$–$R_4$ and optional substituents on ring A have meaning as defined hereinabove, T" is oxo or T" is reactive esterified hydroxy together with hydrogen or lower alkyl; and, if required, reducing the resulting product; or (l) cyclizing a compound of formula XV

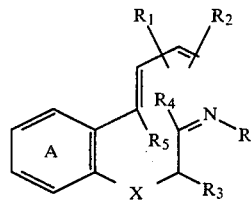

wherein X, R, $R_1$–$R_5$ and optional substituents on ring A have meaning as defined hereinabove to a compound of formula Ib; or (m) cyclizing a compound of the formula XVI

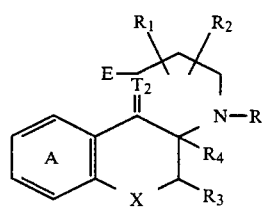

wherein X, R, $R_1$–$R_4$, optional substituents on ring A have meaning as defined hereinabove; $T_2$ is oxo and E represents a removable carbanion stabilizing group; and, if required, reducing the resulting product; and carrying out the said processes while, if necessary, temporarily protecting any interfering reactive group(s) in all these processes, and then isolating the resulting compound of the formula I, IA or IB; and, if desired, converting a resulting compound of formula a I, IA or IB into another compound of the invention, and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

A reactive esterified hydroxy group in any of the above mentioned processes is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example phenylsulfonyloxy or 4-methylphenylsulfonyloxy (tosyloxy).

In starting compounds and intermediates therefor which are converted to the compounds of the invention in a manner described herein, functional groups present, such as carbonyl (formyl or keto), carboxy, amino, hydroxy and sulfhydryl groups, are optionally protected by conventional protecting groups that are common in preparative organic chemistry. Protected carbonyl, carboxy, amino, hydroxy and sulfhydryl groups are those that can be converted under mild conditions into free carbonyl, carboxy, amino, hydroxy and sulfhydryl groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

The preparation of compounds of the invention according to process (a) is carried out according to methods well-known in the art for the reduction of double bonds, e.g. for the compounds of formula IV wherein X represents oxygen, with hydrogen under hydrogenation conditions, preferably in the presence of a catalyst such as palladium on charcoal or, when the compound to be reduced represents an enamine, with a chemical reducing agent such as sodium cyanoborohydride under conditions well-known in the art, at room or elevated temperature in a polar solvent such as isopropanol.

The preparation of compounds of the invention according to process (b) is carried out preferably by reduction with a simple or complex metal hydride reducing agent, advantageously in the presence of a Lewis acid, e.g. with lithium aluminum hydride or sodium borohydride in the presence of boron trifluoride or aluminum chloride.

The preparation according to process (c) is preferably carried out by reduction with a simple or complex hydride reducing agent known in the art for reduction of an amide function e.g. lithium aluminum hydride or borane in an inert solvent such as tetrahydrofuran or diethyl ether, advantageously at room or elevated temperature. The double bond may be reduced simultaneously, if an enamine, or subsequently as described under (a) above.

The process according to process (d) is carried out according to methods well-known in the art for the reduction of pyridine and pyridinium compounds, e.g. advantageously by catalytic hydrogenation to the compounds of formula I, or advantageously by reduction with complex metal hydrides, such as sodium borohydride or aluminum hydride to the compounds of formula Ia or Ib.

The preparation of compounds of the invention according to process (e) comprising reduction to the alcohol and elimination thereof to obtain compounds of formula Ia is carried out e.g. by hydrogenation, e.g. with Adams catalyst in acetic acid, or by treatment with a complex metal hydride reducing agent such as lithium aluminum hydride in pyridine, tetrahydrofuran or ether, or sodium borohydride in methanol.

The compounds of formula I advantageously those wherein X is oxygen, are also prepared from compounds of formula VIII wherein $Y_2$ represents oxo protected in the form of a thioketal by desulfurization with e.g. Raney nickel in alcohol at elevated temperature.

The preparation of compounds of the invention according to process (f) to obtain compounds of formula Ib is carried out as described under process (e) above.

The preparation of compounds of the invention, of formula Ia according to process (g), is carried out by treating a compound of formula X with a halogen, preferably bromine in an inert solvent such as ethyl acetate at a temperature range of 0° to 100° C., and subsequently with a base, advantageously a tertiary amine such as triethylamine or pyridine.

The preparation of compounds of the invention according to process (h) is carried out in a conventional manner, usually in the presence of a solvent or mixture of solvents, and, if necessary, whilst cooling or heating, for example at a temperature range of from approximately −20° C. to approximately 150° C., and/or in an inert gas atmosphere, for example a nitrogen atmosphere. The reaction is carried out advantageously in the presence of a base, such as an inorganic base, for example an alkali metal or alkaline earth metal carbonate, hydride or hydroxide, or in the presence of an organic base, such as an alkali metal lower alkoxide, or a tertiary amine such as triethylamine or pyridine.

The preparation of compounds of the invention by cyclization process (i) by reductive N-alkylation when T represents oxo is carried out under conditions known to the art, e.g. by catalytic hydrogenation with hydrogen in the presence of platinum, palladium or nickel catalysts or with chemical reducing agents such as simple or complex light metal hydrides, advantageously an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid and is advantageously used if a double bond is present in the starting material.

The process according to process (i) when T represents reactive esterified hydroxy together with hydrogen or lower alkyl is carried out with or without basic catalysts such as triethylamine or potassium carbonate in an inert solvent, as is well-known in the art for N-alkylation reactions.

The preparation according to cyclization process (j) is also carried out as described under process (i) above.

Cyclization process (k) is preferably carried out in the presence of a protic acid such as polyphosphoric acid or a Lewis acid such as boron trifluoride or aluminum chloride under conditions well-known in the art for Friedel-Crafts alkylation reactions with or without a suitable organic anhydrous solvent. Using starting materials of formula XIV wherein T" represents oxo, compounds of the invention of formula Ia are obtained. In the case where T" represents reactive esterified hydroxy together with hydrogen or lower alkyl, compounds of formula I are obtained.

The cyclization according to process (l) is carried out in the presence of a strong base such as lithium diisopropylamide or lithium amide in a polar solvent such as tetrahydrofuran preferably at room temperature or lower.

In the cyclization process according to process (m) the removable carbanion stabilizing group in a starting material of formula XVI is for example a triarylphosphoranylidene or di-lower alkylphosphono group, e.g. triphenylphosphoranylidene or diethylphosphono. Said cyclization is carried out under the general conditions of a Wittig reaction in the presence of a strong base, such as sodium hydride in a solvent such as methylene chloride or toluene, at a temperature preferably from −10° to +50° C.

The compounds of formula I wherein R₁ represents carboxy, lower alkoxycarbonyl, carbamoyl or mono- or di-lower alkylcarbamoyl, may also be prepared by cyclization of a compound of the formula XVII

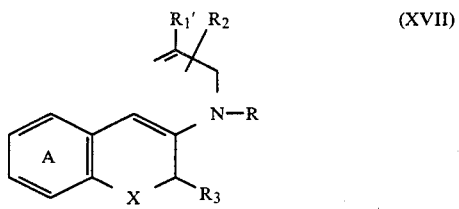

wherein X, R, R₂, R₃ and optional substituents on ring A have meaning as defined hereinabove; R₁' represents carboxy, lower alkoxycarbonyl, carbamoyl or mono- or di-lower alkylcarbamoyl.

Said cyclization may be carried out by heating said starting material of formula XVII in an inert solvent such as toluene, and reducing the double bond in the resulting 4a,10b-dehydro tricyclic product using methods described hereinabove.

The starting materials of formula XVII may be prepared in situ by condensing together the appropriately substituted 2H-[1]-benzopyran-3-one with the appropriately substituted α-aminomethylacrylic acid derivative.

The 2H-[1]-benzopyran-3-ones (chroman-3-ones) are known in the art or are prepared by methods well-known in the art, e.g. as described in J. Chem. Soc. 1610 (1948). The preparation of thiochroman-3-ones is similarly described in the art, e.g. in J. Org. Chem. 34, 1566 (1969).

The starting materials of formula IV–XVI are also prepared by application of methodology generally known in the art.

The compounds of formula IA (also representing starting materials for the preparation of compounds of formula I by process (a) are preferably prepared by process illustrated below for the compounds of formula IA wherein X represents oxygen. The corresponding compounds wherein X represents sulfur are similarly prepared.

The first process involves the intramolecular cyclization of process (g) described hereinabove. The starting materials of formula X for said process are prepared by cyclization of e.g. an N-acyl-6-(optionally substituted phenoxy)-4-hexynylamine, e.g. of 1-phthalimido-6-(optionally substituted phenoxy)-4-hexynylamine in the presence of an organic base such as diethylaniline in a polar solvent such as N,N-dimethylformamide or N-methylpyrrolidone, preferably at elevated temperature, advantageously at a range of 150°–250° C., and subsequent deprotection of the amino protecting group, e.g. with hydrazine in the case where the amino group is protected in form of a phthalimido group, to give the optionally substituted 4-(3-aminopropyl)-2H[1]-benzopyran of formula X (wherein X represents oxygen).

The intermediate 4-hexynylamine derivative is prepared, for example, by condensation of an optionally substituted phenyl propargyl ether with a reactive derivative of 1,3-dihydroxypropane, e.g. 3-bromo-1-chloropropane in the presence of a strong base such as n-butyl lithium and subsequent treatment with e.g. a derivative of ammonia, such as potassium phthalimide.

The compounds of formula IA wherein X represents sulfur may be similarly prepared from the corresponding N-acyl-6-(optionally substituted-phenylthio)-4-hexynylamine.

The compounds of formula IA wherein X represents oxygen are also prepared by condensation of an optionally substituted 2H-[1]-benzopyran-3-one (chroman-3-one) with e.g. an optionally substituted carboxy-protected 3-aminopropanoic acid, e.g. an optionally substituted lower alkyl ester of 3-aminopropanoic acid, e.g. in the presence of an organic acid such as trifluoroacetic acid in an inert solvent such as toluene to give a compound of formula XVIII

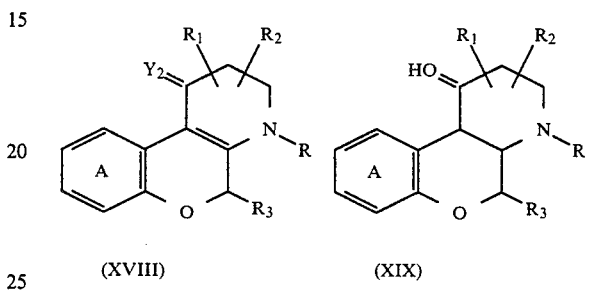

wherein Y₂ represents oxygen, R, R₁–R₃ and optional substituents on ring A have meaning as defined hereinabove.

The compounds of formula XVIII are reduced with a reducing agent such as a complex metal hydride, e.g. lithium aluminum hydride in solvents such as pyridine, diethyl ether and tetrahydrofuran to an alcohol of formula XIX above wherein R–R₃ have meaning as previously defined. Dehydration under conditions well-known in the art yields a corresponding compound of formula IA and/or IB depending on the reaction conditions used. For example, dehydration with phosphorus oxychloride or a mineral acid yields predominantly compounds of formula IA.

The compounds of formula IA or IB wherein X represents sulfur are similarly prepared from the corresponding thiochroman-3-ones.

The compounds of formula XVIII wherein Y₂ represents oxo may also be first reduced selectively to the corresponding 4a,10-b-dihydro derivative by reduction with a metal hydride such as lithium aluminum hydride in pyridine, converted to a thioketal and desulfurized with e.g. Raney nickel.

The compounds of formula IA or IB are converted to the compounds of the invention of formula I by methods well-known in the art for the saturation of double bonds, e.g. by catalytic hydrogenation, e.g. with hydrogen in the presence of a hydrogenation catalyst, such as palladium, in a polar solvent, such as ethanol, at atmospheric or superatmospheric pressure; said saturation of double bond may also be carried out by metal reduction with an alkali metal, such as sodium in a polar solvent, e.g. liquid ammonia and tetrahydrofuran, under conditions well-known in the art.

Compounds of formula IA, especially the compounds wherein R represents lower alkyl, may be converted to compounds of formula IB wherein R₅ represents lower alkyl by treatment with a strong base, e.g. butyl lithium followed by a reactive ester of a lower alkanol, e.g. a lower alkyl halide.

Treatment of a compound of formula IA with a strong base such as butyl lithium followed by a reactive derivative of carbonic acid, e.g. a diester such as a di-lower alkyl carbonate, for example diethyl carbonate, a halocarbonic acid ester, for example ethyl chlorocarbonate, an alkali metal cyanate or lower alkyl isocyanate and, if required, hydrolyzing or N-alkylating the resulting product, yields compounds of formula IA wherein $R_1$ located at the 2-position represents e.g. carboxy, lower alkoxycarbonyl, carbamoyl, mono- or di-lower alkylcarbamoyl. Said compounds may also be converted to the corresponding compounds of formula I by methods described hereinabove.

The starting materials of formula V, for process (b), for example those with a 4a,10b-double bond, may be prepared by condensation of an optionally substituted phenol (or thiophenol) with a lower alkyl ester of 3-piperidone-2-carboxylic acid in the presence of a strong anhydrous acid, e.g. concentrated sulfuric acid.

The starting materials of formula VI, e.g. those wherein Y represents oxo, $Y_1$ represents two hydrogens with a 4a,10b-double bond may be prepared by condensation of an enamine derivative of the optionally substituted chroman-3-one or thiochroman-3-one with an optionally substituted acrylamide e.g. as described in J. Med. Chem. 19, 987 (1976).

Starting materials of formula VII for process (d) may be prepared by condensation e.g. of an optionally substituted o-halophenol (or thiophenol) with a 3-halo-2-halomethylpyridine in a basic medium followed by an Ullmann type reaction in the presence of copper, and finally optional quaternization with e.g. a lower alkyl halide.

Starting materials of formula VIII for process (e) may be prepared as previously illustrated for a compound of formula XVIII by condensation of the appropriately substituted chroman-3-one or thiochroman-3-one with an optionally substituted and protected 3-aminopropanoic acid in the presence of an acid catalyst.

The starting materials of formula IX for process (f) may be prepared by condensation e.g. of an optionally substituted 3-halochroman-4-one (or thiochroman-4-one) with an appropriately substituted and protected 1-aminopropanone (e.g. as a ketal), subsequent deprotection and cyclization according to general methodology as described in J. Organic Chemistry 44, 1108 (1979) to give a compound of formula IX having a 1,10b-double bond.

The preparation of the starting materials of formula X for process (g) has been described above. Said starting materials may also be prepared from the compounds of formula XII wherein T represents hydroxy or reactive esterified hydroxy under elimination conditions well-known in the art.

The starting materials of formula XI for process (h) may be prepared by condensation of e.g. a Grignard reagent prepared from the appropriately substituted and protected o-halophenol or o-halothiophenol with the appropriately substituted and protected 1,4,5,6-tetrahydropyridine-2-carboxylic acid to obtain the corresponding substituted and protected 3-(o-hydroxy- or mercaptophenyl)-piperidine-2-carboxylic acid which is reduced to the correspondingly substituted 3-(o-hydroxy- or mercaptophenyl)-2-hydroxymethylpiperidine. The 3-(o-hydroxy- or mercaptophenyl)-2-hydroxymethylpiperidine is then converted to a corresponding reactive ester, e.g. a chloro or mesyloxy derivative.

The starting materials of formula XII for process (i), e.g. those wherein T represents oxo may be prepared by alkylation of an enamine derivative of the optionally substituted chroman-3-one or thiochroman-3-one with an appropriately substituted reactive 3-(esterified hydroxy)propylamine derivative e.g. an optionally substituted 3-halopropylamine. Said compounds may then be reduced and converted to the corresponding compounds of formula XI wherein T represents reactive esterified hydroxy.

For the preparation of the starting materials for process (j) of formula XIII wherein T' represents oxo, an appropriately substituted chroman-3-one or thiochroman-3-one is first condensed with e.g. a 3-halosubstituted propionaldehyde, protected in the form of an acetal, under basic conditions. The resulting product is reacted with ammonia, a lower alkylamine or an aryl-lower alkylamine under conditions of reductive amination and deprotected by acid treatment.

The starting materials of formula XIII wherein T' represents reactive esterified hydroxy may be prepared by first alkylating an enamine derivative of optionally substituted chroman-3-one or thiochroman-3-one, e.g. with a reactive esterified derivative of 1,3-dihydroxypropane, e.g. 1-bromo-3-chloropropane, and reductively aminating the resulting substituted 3-chromanone with ammonia, a lower alkylamine, or an aryl-lower alkylamine.

The starting materials for process (k) of formula XIV may be prepared by condensation of an optionally substituted phenol or thiophenol with e.g. an optionally substituted reactive ester of 2-hydroxymethyl-3-oxopiperidine such as the chloro or mesyloxy derivative.

The starting materials for process (l) of formula XV may be prepared by condensation of an optionally substituted o-(butadienyl)-phenoxyacetaldehyde with ammonia, a lower alkylamine or an aryl-lower alkylamine. The starting material may be obtained from the appropriately protected o-hydroxybenzaldehyde by Wittig condensation with 3-triphenylphosphoranylidene-1-propene, deprotection, and subsequent condensation with e.g. 2-bromoacetaldehyde diethylacetal.

The compounds of the invention obtained by any of the methods described above can be converted into each other according to conventional methods known to the art, and e.g. as illustrated herein.

Compounds of formula I, Ia or Ib wherein R represents hydrogen, may be converted to the compounds of formula I, Ia or Ib wherein R represents lower alkyl or aryl-lower alkyl by reaction with a reactive esterified lower alkanol or aryl-lower alkanol, e.g. a halide, thereby preferably isolating the resulting compound of formula I, Ia or Ib, as the corresponding acid-addition salt, or by reductive alkylation, e.g. with formaldehyde and formic acid to yield the compound wherein R represents methyl, or with a lower alkyl or aryl-lower alkyl carboxaldehyde in the presence of a reducing agent such as sodium cyanoborohydride.

Compounds of formula I, Ia or Ib wherein R represents lower alkyl, advantageously wherein R represents methyl, can be converted to compounds of formula I, Ia or Ib, wherein R represents hydrogen by catalytic air oxidation, e.g. with palladium or charcoal using an alcohol such as methanol as the solvent, preferably at room temperature, or by reacting with lower alkyl haloformates, e.g. ethyl chloroformate, to yield N-acyl derivatives which, in turn, may be hydrolyzed to said unsubstituted compounds, those with R being hydrogen, for example with a base, such as an alkali metal hydroxide, e.g. an aqueous or hydroalcoholic solution of sodium hydroxide.

Compounds of formula I wherein R is methyl can be prepared by reacting the corresponding compounds of formula I wherein R represents hydrogen with a lower alkyl- or phenyl lower alkyl- haloformate, such as ethyl chloroformate, to obtain compounds of formula I wherein R is alkoxycarbonyl or phenylalkyloxy-carbonyl, and reducing said acyl derivatives with simple or complex light metal hydrides such as lithium aluminum hydride, sodium tri-t-butoxy- or bis-(2-methoxyethoxy)-aluminum hydride.

Compounds of formula I, Ia or Ib wherein ring A is substituted e.g. by acyloxy, such as lower alkanoyloxy or aroyloxy, may be converted to compounds of formula I, Ia or Ib, wherein ring A is substituted by hydroxy by hydrolysis with e.g. aqueous acid, such as hydrochloric acid, or with aqueous alkali, such as lithium or sodium hydroxide.

Conversely, the conversion of compounds of formula I, Ia or Ib wherein e.g. ring A is substituted by hydroxy to compounds of formula I, Ia or Ib, wherein ring A is substituted by acyloxy, such as alkanoyloxy or aroyloxy may be carried out by condensation with a corresponding carboxylic acid, or reactive derivative thereof, according to acylation (esterification) procedures well-known to the art.

The conversion of the compounds of formula I, Ia and Ib wherein ring A is substituted by etherified hydroxy, e.g. lower alkoxy, to the compounds of formula I, Ia or Ib wherein ring A is substituted by hydroxy is carried out by methods well-known in the art, e.g., with a mineral acid, such as hydriodic acid or, advantageously for compounds wherein the lower alkoxy is methoxy, with e.g. boron tribromide in methylene chloride or with sodium or lithium diphenylphosphide in tetrahydrofuran.

The conversion of compounds of formula I, Ia or Ib wherein ring A is substituted by optionally substituted benzyloxy to compounds of formula I, Ia or Ib wherein ring A is substituted by hydroxy is advantageously carried out by hydrogenolysis using hydrogen in the presence of a catalyst e.g. palladium.

Compounds of formula I, Ia or Ib wherein R represents benzyl or optionally substituted benzyl, may be hydrogenolyzed to the corresponding compounds wherein R represents hydrogen for example with hydrogen in the presence of a hydrogenolysis catalyst, e.g. palladium on charcoal.

Unsaturated compounds, such as those bearing an alkenyl or alkynyl radical, may also be hydrogenated with catalytically activated hydrogen to obtain compounds of formula I or intermediates bearing the corresponding alkyl radical.

The unsaturated compounds of formula Ia or Ib may be converted to the saturated compounds of formula I by reduction methods described hereinabove and illustrated in the examples.

With reference to the above reactions and as mentioned above, it may be advantageous to appropriately protect the potentially reactive, e.g. amino, carboxy, hydroxy, or other interfering substituents in accordance with protective techniques well-known to the art, e.g. as illustrated below, such that interfering reactions are avoided, by protecting such substituents prior to the desired reaction and subsequently, if necessary removing the protective groups to obtain the desired compounds, e.g. of formula I, or intermediates.

For instance, a free basic amino group, bearing at least one hydrogen on nitrogen, may be protected in the form of easily cleaved amides, e.g. as acyl derivatives such as the benzyloxycarbonyl (carbobenzyloxy) or the t-butyloxycarbonyl derivatives, or any other easily removable N-protecting group.

A carboxy group may be protected in the form of an easily cleaved ester, e.g. the benzyl ester, the t-butyl ester, and the like as commonly used.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

In a resulting protected compound of formula I or intermediate, in which one or more of the functional groups are protected, the protected functional groups, e.g. amino, hydroxy or carboxy groups can be liberated, in a manner, known per se, e.g. by means of solvolysis, especially hydrolysis with acid, or by means of reduction, especially hydrogenolysis.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being preferred.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds or intermediates are obtained, these can be separated into the single racemic or optically active isomers by methods in themselves known, e.g. by fractional distillation, crystallization and/or chromatography.

Compounds of formula I, II or III with a trans-4a,10b-ring junction may be prepared from compounds of formula I, II or III with a cis-4a,10b-ring junction by treatment with a strong base, such as potassium t-butoxide, in a non-aqueous solvent, such as dimethylsulfoxide, and if required, separating the trans fused compound from a mixture of isomers by e.g. chromatography or crystallization.

The racemic products of formula I, Ia or Ib, or basic intermediates can be resolved into the optical antipodes, for example, by separation of diastereomeric salts thereof, e.g., by the fractional crystallization of d- or l-(tartrate, dibenzoyltartrate, mandelate or camphorsulfonate)salts.

Any acidic intermediates can be resolved by separation of e.g. the d- and l-(α-methylbenzylamine, cinchonidine, cinchonine, quinine, quinidine, ephedrine, dehydroabietylamine, brucine or strychnine)-salts of any compounds having an acidic salt-forming group.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention additionally relates to the use in mammals of the compounds of formula I, Ia or Ib and their pharmaceutically acceptable, non-toxic acid addition salts, or pharmaceutical compositions thereof, as medicaments, especially as psychotropic agents for the treatment of central nervous system disorders responsive to the modulation of psychotropic central nervous system receptors, such as presynaptic dopamine receptor stimulation or serotonin receptor stimulation, e.g. as neuroleptic (antipsychotic) agents for the treatment of psychotic conditions or antidepressant agents for the treatment of depression.

The present invention also relates to the use of the compounds of the invention for the preparation of pharmaceutical compositions, especially pharmaceutical compositions having psychotropic receptor modulating activity, e.g. presynaptic dopamine receptor or serotonin receptor modulating, especially stimulating activity.

The pharmaceutical compositions according to the invention are those suitable for enteral, such as oral or rectal, transdermal and parenteral administration to mammals, including man, for the treatment of diseases responsive to e.g. presynaptic dopamine receptor stimulation, such as psychotic disorders, or serotonin receptor stimulation, such as depression comprising an effective amount of a pharmacologically active compound of formula I, Ia or Ib or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethyleneglycol; for tablets also (c) binders, e.g. magnesium alumnium silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I, Ia or Ib with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

More specifically, the invention also relates advantageously to the method of treatment of psychotropic disorders in mammals e.g. such responsive to presynaptic dopamine receptor stimulation or to serotonin receptor stimulation, using an effective amount of a compound of the invention, e.g. of formula I, Ia, or Ib, or pharmaceutically acceptable salts of such compounds as pharmacologically active substances, preferably in the form of above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degress Centigrade. If not mentioned otherwise, all evaporations are performed under reduced pressure, preferably between about 15 and 100 mm Hg.

EXAMPLE 1

To a solution of 9.0 g of 9-methoxy-4-propyl-1,2,3,5-tetrahydro-4H-[1]-benzopyrano[3,4-b]pyridin-1-one in 90 ml of dry pyridine at 0° is added 0.90 g of lithium aluminium hydride. After 20 minutes at 30° the reaction is quenched with 1.8 ml of 10% sodium hydroxide, the reaction mixture is diluted with ethyl acetate, dried over magnesium sulfate and filtered. The filter cake is washed well with 10% methanol/methylene chloride and the solvent is removed in vacuo from the combined filtrates. The entire above reduction procedure is repeated on the residue using tetrahydrofuran instead of pyridine as the initial reaction solvent. The product is triturated with ether to afford a white powder which is treated with 28 ml of pyridine and 6.3 ml of phosphorus oxychloride at 65° for 30 minutes. The reaction mixture is poured onto a mixture of ice and sodium carbonate solution, and the product is extracted with ethyl acetate. After drying over magnesium sulfate, the solvent is removed in vacuo to afford, as an oil, 9-methoxy-4-propyl-2,3,4a,5-tetrahydro-4H-[1]-benzopyrano[3,4-b]pyridine; NMR: $\delta$ 0.90 (3H,t), 3.75 (3H,s).

The starting material is prepared as follows: To a well stirred solution of 60 g of 6-methoxy-2H-[1]-benzopyran [J. Org. Chem. 39, 881 (1974)] in 300 ml of acetone and 150 ml of water is added 70 g of N-bromosuccinimide in portions over 5 minutes. After 10 minutes at room temperature, the reaction mixture is diluted with water and the product is extracted with ether. After washing the combined ether fraction with water, it is dried over magnesium sulfate and the solvent removed in vacuo. The crystalline residue is triturated with ether/hexane to afford trans-3-bromo-4-hydroxy-6-methoxy-3,4-dihydro-2H-[1]-benzopyran, m.p. 98°–99°.

To a suspension of 2.0 g sodium hydride in 100 ml of dry tetrahydrofuran is added with stirring a solution of 20 g of trans-3-bromo-4-hydroxy-6-methoxy-3,4-dihydro-2H-[1]-benzopyran in 200 ml of dry tetrahydrofuran in a dropwise fashion. After 30 minutes stirring at room temperature, the reaction mixture is filtered through filter-cel and the solvent is removed in vacuo. The residue is dissolved in 100 ml of toluene, 1.0 g of anhydrous zinc iodide is added and the mixture is heated at 80° for 1 hour. The reaction mixture is filtered through 120 g of silica gel with methylene chloride as the eluent to afford a product which is recrystallized from ether to give 6-methoxy-2H-[1]-benzopyran-3-one, m.p. 67°–72°.

A mixture of 8.9 g of 6-methoxy-2H-[1]-benzopyran-3-one, 7.46 g of methyl 3-(propylamino)-propionate, 0.8 ml of trifluoroacetic acid in 80 ml toluene is refluxed for 7 hours in a Dean Stark apparatus; additional 0.8 ml portions of trifluoroacetic acid are added at 2, 4 and 6 hours. The reaction mixture is cooled and the solvent is removed in vacuo. The residue is crystallized from ether/methanol to afford 9-methoxy-4-propyl-1,2,3,5-tetrahydro-4H-[1]-benzopyrano[3,4-b]pyridin-1-one, m.p. 97°–100°.

EXAMPLE 2

(a) To a solution of 6.8 g of 9-methoxy-4-propyl-2,3,4a,5-tetrahydro-4H-[1]-benzopyrano[3,4-b]pyridine in 50 ml of tetrahydrofuran and 200 ml of liquid ammonia is added 0.45 g of water followed by 2.8 g of sodium at −70°. The mixture is stirred for 5 minutes at −33°, after which time a persistant blue color is obtained. The mixture is quenched with excess ammonium chloride and the ammonia is allowed to evaporate. After dilution with water, the products are extracted with ether, the organic phase is dried and the solvent is removed in vacuo. The crude product is dissolved in ethanol, treated with excess ethanolic hydrogen chloride and cooled to crystallize the salt which is collected to afford trans-9-methoxy-4-propyl-1,2,3,4a,5,10b-hexahydro-4H-[1]-benzopyrano-[3,4-b]pyridine hydrochloride, m.p. 252°–254°.

(b) The mother liquor from the above crystallization is evaporated to dryness to yield cis-9-methoxy-4-propyl-1,2,3,4a,5,10b-hexahydro-4H-[1]-benzopyrano[3,4-b]pyridine hydrochloride, m.p. 200°–202°.

EXAMPLE 3

To a solution of 5.0 g of 9-methoxy-4-propyl-2,3,4a,5-tetrahydro-4H-[1]-benzopyrano[3,4-b]pyridine in 150 ml of dry tetrahydrofuran is added 8.8 ml of 2.2M butyllithium in hexane at −78°. The resulting orange solution is stirred for 30 minutes at 0°. After cooling to −78°, 3.0 g of methyl iodide is added and again the reaction mixture is stirred for 30 minutes at 0°. After pouring the reaction mixture onto water the products are extracted with ether, the organic layer is dried and the solvent removed in vacuo. Chromatography on 400 g silica gel (ether-hexane, 1:4) affords in succession:
(a) cis 9-methoxy-2-methyl-4-propyl-2,3,4a,5-tetrahydro-4H-[1]-benzopyrano[3,4-b]pyridine,
(b) cis and trans-9-methoxy-10b-methyl-4-propyl-3,4a,5,10b-tetrahydro-4H-[1]-benzopyrano[3,4-b]pyridine and
(c) trans-9-methoxy-2-methyl-4-propyl-2,3,4a,5-tetrahydro-4H-[1]-benzopyrano[3,4-b]pyridine (trans as to 2 and 4a positions).
Similarly prepared are:
(d) cis and trans-7-methoxy-4,10b-dimethyl-3,4a,5,10b-tetrahydro-4H-[1]-benzopyrano[3,4-b]pyridine.
(e) cis and trans-7-methoxy-2,4-dimethyl-2,3,4a,5-tetrahydro-4H-[1]-benzopyrano[3,4-b]pyridine.

EXAMPLE 4

(a) To a solution of 4.5 g of trans-9-methoxy-4-propyl-1,2,3,4a,5,10b-hexahydro-4H-[1]-benzopyrano[3,4-b]pyridine in 30 ml of hot isopropanol is added 6.48 g of (−)-dibenzoyltartaric acid monohydrate. Cooling affords a white crystalline dibenzoyltartrate salt which is recrystallized three times from ethanol to a constant melting point of 174°–175°. The salt is converted to the free base by partitioning between ether and dilute sodium bicarbonate solution, drying the ether extract over magnesium sulfate and removing the solvent to afford (+)-trans-9-methoxy-4-propyl-1,2,3,4a,5,10b-hexahydro-4H-[1]-benzopyrano[3,4-b]pyridine, as an oil, $[\alpha]_D^{25}+71.97°$ (c=1.0, 0.1N hydrochloric acid).

(b) The combined mother liquors of the ethanol recrystallizations under (a) are evaporated to dryness and the residual salts are converted to the free base as described under (a). Treatment with an equivalent quantity of (+)-dibenzoyltartaric acid monohydrate in isopropanol gives a salt which is recrystallized three times from ethanol to give the optically active salt, melting point 176°–178°. Reconversion to the free base as described under (a) yields (−)-trans-9-methoxy-4-propyl-1,2,3,4a,5,10b-hexahydro-4H-[1]-benzopyrano[3,4-b]pyridine, as an oil, $[\alpha]_D^{25}-70.26°$ (c=1.0, 0.1N hydrochloric acid).

EXAMPLE 5

(a) To a solution of lithium diphenyl phosphide prepared from 4.27 g of diphenyl phosphine and 8.9 ml of 2.2M butyllithium in hexane in 30 ml of dry tetrahydrofuran is added 3.0 g of trans-9-methoxy-4-propyl-1,2,3,4a,5,10b-hexahydro-4H-[1]-benzopyrano[3,4-b]pyridine and the mixture is refluxed for 5 hours. The reaction mixture is diluted with ether and the product is extracted with 2N hydrochloric acid. After neutralization of the aqueous phase with sodium carbonate, the product is extracted with ethyl acetate, the organic layer dried over magnesium sulfate and the solvent removed in vacuo. The residue is dissolved in hot ethanol, and an excess of a 5.4M solution of hydrogen chloride in ethanol is added. Cooling leads to crystallization of trans-9-hydroxy-4-propyl-1,2,3,4a,5,10b-hexahydro-4H-[1]-benzopyrano[3,4-b]pyridine hydrochloride, m.p. 292°–294°.

(b) Similarly (+)-trans-9-methoxy-4-propyl-1,2,3,4a,5,10b-hexahydro-4H-[1]-benzopyrano[3,4-b]pyridine yields (+)-trans-9-hydroxy-4-propyl-1,2,3,4a,5,10b-hexahydro-4H-[1]-benzopyrano[3,4-b]pyridine hydrochloride, $[\alpha]_D^{25}+81.79°$ (c=1.0, water), m.p. 292° (dec).

(c) Similarly (−)-trans-9-methoxy-4-propyl-1,2,3,4a,5,10b-hexahydro-4H-[1]-benzopyrano[3,4-b]pyridine yields (−)-trans-9-hydroxy-4-propyl-1,2,3,4a,5,10b-hexahydro-4H-[1]-benzopyrano[3,4-b]pyridine hydrochloride, $[\alpha]_D^{25}-80.35°$ (c=1.0, water), m.p. 292° (dec).

(d) Similarly 9-methoxy-4-propyl-2,3,4a,5-tetrahydro-4H-[1]-benzopyrano[3,4-b]pyridine yields 9-hydroxy-4-propyl-2,3,4a,5-tetrahydro-4H-[1]-benzopyrano[3,4-b]pyridine hydrochloride, m.p. 265°–266°.

(e) Similarly cis and trans-9-methoxy-2-methyl-4-propyl-2,3,4a,5-tetrahydro-4H-[1]-benzopyrano[3,4-b]pyridine yield cis and trans-9-hydroxy-2-methyl-4-propyl-2,3,4a,5-tetrahydro-4H-[1]-benzopyrano[3,4-b]pyridine hydrochloride, m.p. 248°–250° and m.p. 237°–240° respectively.

EXAMPLE 6

(a) A solution of 1.5 g of a mixture of cis and trans-9-methoxy-10b-methyl-4-propyl-3,4a,5,10b-tetrahydro-4H-[1]-benzopyrano[3,4-b]pyridine (Example 3b) in 30 ml of ethanol is hydrogenated at 3 atm. pressure in the presence of 500 mg of 10% palladium on charcoal catalyst for 3 hours to give cis and trans-9-methoxy-10b-methyl-4-propyl-1,2,3,4a,5,10b-hexahydro-4H-[1]-benzopyrano[3,4-b]pyridine as a mixture of isomers.

(b) The product from (a) is then heated under reflux for 5 hours with a solution of 1.85 g of diphenylphosphine and 3.85 ml of 2.2M n-butyllithium in 15 ml of tetrahydrofuran. The products are extracted with 3N aqueous hydrochloric acid, the aqueous layer is neutralized with base and extracted with chloroform. After drying over magnesium sulfate, the solvent is removed in vacuo and the residue chromatographed on 60 g of silica gel with ether/hexane (1:1) as the eluent to give, after conversion to the hydrochloride salt, trans-9-hydroxy-10b-methyl-4-propyl-1,2,3,4a,5,10b-hexahydro-4H-[1]-benzopyrano[3,4-b]pyridine hydrochloride, m.p. 238°–241°, and cis-9-hydroxy-10b-methyl-4-propyl-1,2,3,4a,5,10b-hexahydro-4H-[1]-benzopyrano[3,4-b]pyridine hydrochloride, m.p. 244°–245°.

(c) Similarly, a mixture of cis and trans-7-methoxy-4,10b-dimethyl-3,4a,5,10b-tetrahydro-4H-[1]-benzopyrano[3,4-b]pyridine yields cis- and trans-7-(methoxy and hydroxy)-4,10b-dimethyl-1,2,3,4a,5,10b-hexahydro-4H-[1]-benzopyrano[3,4-b]pyridine; trans-7-hydroxy-4,10b-dimethyl-1,2,3,4a,5,10b-hexahydro-4H-[1]-benzopyrano[3,4-b]pyridine hydrochloride has a m.p. of 252°–253°.

EXAMPLE 7

Prepared essentially according to the procedures described in the previous examples are:

(a) 7-methoxy-4-propyl-2,3,4a,5-tetrahydro-4H-[1]-benzopyrano[3,4-b]pyridine [NMR: δ 0.90 (3H,t) 3.80 (3H,s)] starting from 8-methoxy-2H-[1]-benzopyran [J. Org. Chem. 39, 881 (1974)] via 8-methoxy-2H-benzopyran-3-one, m.p. 78°–80°;

(b) 7-hydroxy-4-propyl-2,3,4a,5-tetrahydro-4H-[1]-benzopyrano[3,4-b]pyridine hydrochloride, m.p. 195°–196°;

(c) trans-7-hydroxy-4-propyl-1,2,3,4a,5,10b-hexahydro-4H-[1]-benzopyrano[3,4-b]pyridine hydrochloride, m.p. 260°–262°;

(d) cis-7-hydroxy-4-propyl-1,2,3,4a,5,10b-hexahydro-4H-[1]-benzopyrano[3,4-b]pyridine hydrochloride, m.p. 220°–223°;

(e) (+)-trans-7-hydroxy-4-propyl-1,2,3,4a,5,10b-hexahydro-4H-[1]-benzopyrano[3,4-b]pyridine hydrochloride, m.p. 283°–286°, $[\alpha]_D^{25}+85.73°$ (c=1.0, water); dibenzoyl-tartrate salt, m.p. 203°–204°;

(f) (−)-trans-7-hydroxy-4-propyl-1,2,3,4a,5,10b-hexahydro-4H-[1]-benzopyrano[3,4-b]pyridine hydrochloride, m.p. 285°–287°, $[\alpha]_D^{25}-88.69$ (c=1.0, water);

(g) 7-methoxy-4-methyl-2,3,4a,5-tetrahydro-4H-[1]-benzopyrano[3,4-b]pyridine hydrochloride, m.p. 236°–239°, by condensation of 8-methoxy-2H-[1]-benzopyran-3-one with ethyl 3-(methylamino)propionate, and subsequent steps analogous to Example 1;

(h) trans-7-methoxy-4-methyl-1,2,3,4a,5,10b-hexahydro-4H-[1]-benzopyrano[3,4-b]pyridine hydrochloride, m.p. 236°–238°;

(i) trans and cis-4-butyl-7-hydroxy-1,2,3,4a,5,10b-hexahydro-4H-[1]-benzopyrano[3,4-b]pyridine hydrochloride, m.p. 252°–253° and 160°–162° respectively, by condensation of 8-methoxy-2H-[1]-benzopyran-3-one with methyl 3-(butylamino)-propionate and subsequent steps analogous to examples 1, 2 and 5;

(j) 9-hydroxy-4-methyl-2,3,4a,5-tetrahydro-4H-[1]-benzopyrano[3,4-b]pyridine hydrochloride, m.p. 265°–268° (dec);

(k) 7-hydroxy-4-methyl-2,3,4a,5-tetrahydro-4H-[1]-benzopyrano[3,4-b]pyridine hydrochloride, m.p. 257°–259°;

(l) 8,9-dihydroxy-4-propyl-2,3,4a,5-tetrahydro-4H-[1]-benzopyrano[3,4-b]pyridine hydrochloride, m.p. 205°–206°;

(m) 4-methyl-2,3,4a,5-tetrahydro-4H-[1]-benzopyrano[3,4-b]pyridine hydrochloride, m.p. 242°–244°;

(n) trans-7-hydroxy-4-methyl-1,2,3,4a,5,10b-hexahydro-4H-[1]-benzopyrano[3,4-b]pyridine hydrochloride, m.p. 275°–277°;

(o) cis-7-hydroxy-4-methyl-1,2,3,4a,5,10b-hexahydro-4H-[1]-benzopyrano[3,4-b]pyridine hydrochloride, m.p. 238°–240°;

(p) trans-9-hydroxy-4-methyl-1,2,3,4a,5,10b-hexahydro-4H[1]-benzopyrano[3,4-b]pyridine hydrochloride, m.p. >260° (dec);

(q) trans-8,9-dihydroxy-4-propyl-1,2,3,4a,5,10b-hexahydro-4H-[1]-benzopyrano[3,4-b]pyridine hydrochloride, m.p. 290° (dec);

(r) 4-benzyl-9-methoxy-2,3,4a,5-tetrahydro-4H-[1]-benzopyrano[3,4-b]pyridine by condensation of 6- methoxy-2H-[1]-benzopyran-3-one with ethyl 3-benzylaminopropionate and subsequent steps analogous to Example 1;
(s) 4-benzyl-9-hydroxy-2,3,4a,5-tetrahydro-4H-[1]-benzopyrano[3,4-b]pyridine;
(t) 4-benzyl-9-methoxy-1,2,3,4a,5,10b-hexahydro-4H-[1]-benzopyrano[3,4-b]pyridine;
(u) 4-benzyl-9-hydroxy-1,2,3,4a,5,10b-hexahydro-4H-[1]-benzopyrano[3,4-b]pyridine.

EXAMPLE 8

To a suspension of 3.0 g of 9-methoxy-4-propyl-1,2,3,5-tetrahydro-4H-[1]-benzothiopyrano[3,4-b]pyridin-1-one in 150 ml of anhydrous ether is added 750 mg of lithium aluminium hydride in one portion. After stirring for 1 hour at room temperature, the reaction mixture is quenched with 1.5 ml of 10% sodium hydroxide, filtered and the filter cake washed well with ether. After removal of solvent, the residue is dissolved in 20 ml of ethanol, 5 ml of acetic acid and 1.5 g of sodium cyanoborohydride are added. After stirring for 2 hours at room temperature, the reaction mixture is poured onto sodium carbonate solution and the products are extracted with ether. After drying the extract, the solvent is removed in vacuo and the residue is chromatographed on 60 g of silica gel with ether/methylene chloride as the eluent to afford in succession:
(a) 9-methoxy-4-propyl-2,3,4a,5-tetrahydro-4H-[1]-benzothiopyrano[3,4-b]pyridine, characterized as hydrochloride salt, m.p. 215°-216°;
(b) cis-9-methoxy-4-propyl-1,2,3,4a,5,10b-hexahydro-4H-[1]-benzothiopyrano[3,4-b]pyridine; and
(c) trans-9-methoxy-4-propyl-1,2,3,4a,5,10b-hexahydro-4H-[1]-benzothiopyrano[3,4-b]pyridine.

The starting material is prepared as follows: A mixture of 7.5 g 6-methoxythiochroman-3-one [J. Org. Chem. 34, 1566 (1969)], 5.8 g of methyl 3-(propylamino)-propionate and 0.8 ml of trifluoroacetic acid in 80 ml of toluene is heated under reflux for 22 hours in a Dean Stark apparatus. Additional 0.8 ml portions of trifluoroacetic acid are added after 2, 5, and 16 hours. The solvent is removed, the residue is taken up in ether and the product is extracted with 3N hydrochlorid acid. After neutralization the aqueous layers are extracted with ethyl acetate, the organic layer is dried and the solvent is removed. The product is crystallized from a small volume of methanol to afford 9-methoxy-4-propyl-1,2,3,5-tetrahydro-4H-[1]-benzothiopyrano[3,4-b]pyridin-1-one, m.p. 108°-110°.

Similarly prepared are:
(d) 4-propyl-2,3,4a,5-tetrahydro-4H-[1]-benzothiopyrano[3,4-b]pyridine hydrochloride, m.p. 231°-235°, starting with thiochroman-3-one;
(e) trans-4-propyl-1,2,3,4a,5,10b-hexahydro-4H-[1]-benzothiopyrano[3,4-b]pyridine hydrochloride;
(f) 7-methoxy-4-propyl-2,3,4a,5-tetrahydro-4H-[1]-benzothiopyrano[3,4-b]pyridine hydrochloride, m.p. 244°-246°, starting with 8-methoxythiochroman-3-one;
(g) trans-7-methoxy-4-propyl-1,2,3,4a,5,10b-hexahydro-4H-[1]-benzothiopyrano[3,4-b]pyridine.

The starting material for the compound of example 8f, 8-methoxythiochroman-3-one, is prepared as follows: To a mixture of 28 g of o-methoxybenzenethiol, 50 g of 45% potassium hydroxide in 70 ml of dimethyl sulfoxide is added 33 g of α-(bromomethyl)-acrylic acid in 30 ml of dimethyl sulfoxide while maintaining the temperature at 50°-60°. After 1 hour the reaction mixture is poured onto dilute hydrochloric acid and the products are extracted with ether. The ether layer is extracted with sodium bicarbonate solution. Acidification of the aqueous bicarbonate extracts affords α-(o-methoxyphenylthiomethyl)acrylic acid, m.p. 101°-104°.

A mixture 22.5 g of α-(o-methoxyphenylthiomethyl)-acrylic acid, 2.53 g of triethylamine and 200 ml of o-dichlorobenzene is heated for 12 hours at 195°. After dilution with ether the products are extracted with sodium bicarbonate solution. Acidification of the basic extracts affords 8-methoxy-3,4-dihydro-2H-[1]-benzothiopyran-3-carboxylic acid, m.p. 138°-144°.

To a solution of 10 g of 8-methoxy-3,4-dihydro-2H-[1]-benzothiopyran-3-carboxylic acid in 200 ml of methylene chloride is added 6.2 g of N-chlorosuccinimide in portions. After 10 minutes 60 g of silica gel is added. The reaction mixture is stirred for 15 minutes, filtered through 40 g of silica gel eluting with ether/methylene chloride (1:1). The solvent is concentrated to 100 ml, 5 ml of triethylamine and 5 g of ethyl chloroformate are added. After concentration 5 g of sodium azide in 60 ml of dimethylformamide are added and the reaction mixture is stirred for 1 hour. After dilution with water the products are extracted with ether, the ether extract is dried and evaporated to dryness; 150 ml of 10% aqueous sulfuric acid is added and the reaction mixture is heated under reflux for 2 hours. The reaction mixture is extracted with ether, the ether extract is washed with dilute sodium bicarbonate solution, dried and evaporated to dryness. Crystallization from methanol affords 8-methoxythiochroman-3-one, m.p. 60°.

EXAMPLE 9

(a) To a solution of 1.8 ml of diphenylphosphine in 25 ml of tetrahydrofuran is added 4.7 ml of 2.1M n-butyllithium in hexane at 0°, followed by 1.3 g of 9-methoxy-4-propyl-2,3,4a,5-tetrahydro-4H-[1]-benzothiopyrano[3,4-b]pyridine. After refluxing for 5 hours under nitrogen, the reaction mixture is diluted with ether and the product is extracted with 10% sodium hydroxide. The aqueous layer is neutralized and the product is extracted with ethyl acetate. After drying, the solvent is removed in vacuo. The residue is dissolved in ethanol, acidified with ethanolic hydrogen chloride and the resulting crystals are collected to afford 9-hydroxy-4-propyl-2,3,4a,5-tetrahydro-4H-[1]-benzothiopyrano[3,4-b]pyridine hydrochloride, m.p. 275°-277°.

Similarly prepared are:
(b) cis-9-hydroxy-4-propyl-1,2,3,4a,5,10b-hexahydro-4H-[1]-benzothiopyrano[3,4-b]pyridine hydrochloride, m.p. 246°-248°;
(c) trans-9-hydroxy-4-propyl-1,2,3,4a,5,10b-hexahydro-4H-[1]-benzothiopyrano[3,4-b]pyridine hydrochloride, m.p. 285°-286°;
(d) 7-hydroxy-4-propyl-2,3,4a,5-tetrahydro-4H-[1]-benzothiopyrano[3,4-b]pyridine hydrochloride, m.p. 225°-228°;
(e) trans-7-hydroxy-4-propyl-1,2,3,4a,5,10b-hexahydro-4H-[1]-benzothiopyrano[3,4-b]pyridine hydrochloride;

EXAMPLE 10

(a) To a solution of 550 mg of trans-9-hydroxy-4-propyl-1,2,3,4a,5,10b-hexahydro-4H-[1]-benzopyrano[3,4-b]pyridine hydrochloride in 10 ml of methylene chloride is added 1.4 g of diisopropylethylamine and 680 mg of benzoyl chloride and the mixture is stirred for 2 hours. After dilution with methylene chloride the reaction mixture is washed with water and saturated sodium bicarbonate, dried over magnesium sulfate and the solvent is removed in vacuo. Addition of sufficient ethanolic hydrogen chloride precipitates trans-9-benzoyloxy-4-propyl-1,2,3,4a,5,10b-hexahydro-4H-[1]-benzopyrano[3,4-b]pyridine hydrochloride, m.p. 238°–240°.

Similarly prepared are:

(b) trans-7-benzoyloxy-4-propyl-1,2,3,4a,5,10b-hexahydro-4H-[1]-benzopyrano[3,4-b]pyridine hydrochloride;

(c) 9-benzoyloxy-4-propyl-2,3,4a,5-tetrahydro-4H-[1]-benzopyrano[3,4-b]pyridine;

(d) trans-9-nicotinoyloxy-4-propyl-1,2,3,4a,5,10b-hexahydro-4H-[1]-benzopyrano[3,4-b]pyridine;

(e) trans-9-pivaloyloxy-4-propyl-1,2,3,4a,5,10b-hexahydro-4H-[1]-benzopyrano[3,4-b]pyridine hydrochloride, m.p. 229°–230°;

(f) trans-9-dimethylaminocarbonyloxy-4-propyl-1,2,3,4a,5,10b-hexahydro-4H-[1]-benzopyrano[3,4-b]pyridine hydrochloride, m.p. 185°–187°;

(g) trans-9-acetoxy-4-propyl-1,2,3,4a,5,10b-hexahydro-4H-[1]-benzopyrano[3,4-b]pyridine hydrochloride;

(h) 9-benzoyloxy-4-propyl-2,3,4a,5,-tetrahydro-4H-[1]-benzothiopyrano[3,4-b]pyridine hydrochloride;

(i) 9-acetoxy-4-propyl-1,2,3,4a,5,10b-hexahydro-4H-[1]-benzothiopyrano[3,4-b]pyridine hydrochloride;

(j) 4-butyl-9-(2-methylpropionyloxy)-1,2,3,4a,5,10b-hexahydro-4H-[1]-benzopyrano[3,4-b]pyridine.

EXAMPLE 11

(a) To a well stirred solution of 1.16 g of 9-methoxy-4-methyl-2,3,4a,5-tetrahydro-4H-[1]-benzopyrano[3,4-b]pyridine in 15 ml of tetrahydrofuran is added 3.4 ml of 1.5M butyllithium in hexane at 0°. After 5 minutes at 0°, the reaction mixture is cooled to −70° and 0.6 ml of t-butyl isocyanate is added. After warming to room temperature the reaction mixture is diluted with water and the products extracted with ether. After drying over magnesium sulfate, the solvent is removed in vacuo and the residue is crystallized from ether/hexane to yield cis-2-(N-t-butylcarbamoyl)-9-methoxy-4-methyl-2,3,4a,5-tetrahydro-4H-[1]-benzopyrano[3,4-b]pyridine, which is converted to ethanolic hydrogen chloride to cis-2-(N-t-butylcarbamoyl)-9-methoxy-4-methyl-2,3,4a,5-tetrahydro-4H-[1]-benzopyrano[3,4-b]pyridine hydrochloride, m.p. 188°–189° (from ethanol/ether).

(b) A solution of 950 mg of cis-2-(N-t-butylcarbamoyl)-9-methoxy-4-methyl-2,3,4a,5-tetrahydro-4H-[1]-benzopyrano[3,4-b]pyridine in 50 ml of 0.1M ethanolic sodium ethoxide is heated at 70° for 15 minutes. After removal of the solvent in vacuo, the residue is chromatographed over 20 g silica gel with ether/hexane 1:1 as the eluent to give trans-2-(N-t-butylcarbamoyl)-9-methoxy-4-methyl-2,3,4a,5-tetrahydro-4H-[1]-benzopyrano[3,4-b]pyridine crystallized as the hydrochloride salt, m.p. 238°–240°.

EXAMPLE 12

(a) To a solution of 500 mg of trans-7-hydroxy-4-methyl-1,2,3,4a,5,10b-hexahydro-4H-[1]-benzopyrano[3,4-b]pyridine in 5 ml of acetic acid is added 365 mg of bromine and the mixture is stirred at room temperature for 4 hours. After dilution with water, neutralization of the aqueous layer, extraction with methylene chloride and drying of the extract over magnesium sulfate, the solvent is removed in vacuo. The residue is dissolved in ethanol and acidified with ethanolic hydrogen chloride to afford trans-8-bromo-7-hydroxy-4-methyl-1,2,3,4a,5,10b-hexahydro-4H-[1]-benzopyrano[3,4-b]pyridine hydrochloride, m.p. 282°–284°.

(b) Similarly, reaction of trans-7-methoxy-4-methyl-1,2,3,4a,5,10b-hexahydro-4H-[1]-benzopyrano[3,4-b]pyridine with 2 equivalents of bromine yields trans-8,10-dibromo-7-methoxy-4-methyl-1,2,3,4a,5,10b-hexahydro-4H-[1]-benzopyrano[3,4-b]pyridine hydrochloride, m.p. 234°–237°.

EXAMPLE 13

(a) To a solution of 219 mg of trans-7-hydroxy-4-methyl-1,2,3,4a,5,10b-hexahydro-4H-[1]-benzopyrano[3,4-b]pyridine in 5 ml tetrahydrofuran and 1 ml of dimethylformamide is added 75 mg of 50% sodium hydride dispersion in mineral oil with stirring; 115 mg of allyl bromide is then added and the mixture is stirred for 3 hours at reflux. After dilution with ether, the reaction mixture is washed with water and dried over magnesium sulfate and the solvent is removed in vacuo. The residue is dissolved in ethyl acetate and treated with ethanolic hydrogen chloride to afford trans-7-allyloxy-4-methyl-1,2,3,4a,5,10b-hexahydro-4H-[1]-benzopyrano[3,4-b]pyridine hydrochloride, m.p. 229°–230°.

Similarly prepared as:

(b) trans-9-benzyloxy-4-propyl-1,2,3,4a,5,10b-hexahydro-4H-[1]-benzopyrano[3,4-b]pyridine by alkylating trans-9-hydroxy-4-propyl-1,2,3,4a,5,10b-hexahydro-4H-[1]-benzopyrano[3,4-b]pyridine with benzyl bromide;

(c) trans-9-propargyloxy-4-propyl-1,2,3,4a,5,10b-hexahydro-4H-[1]-benzopyrano[3,4-b]pyridine;

(d) trans-7-butoxy-4-propyl-2,3,4a,5-tetrahydro-4H-[1]-benzopyrano[3,4-b]pyridine;

(e) 7-allyloxy-4-propyl-2,3,4a,5-tetrahydro-4H-[1]-benzothiopyrano[3,4-b]pyridine;

(f) trans-9-ethoxy-4-propyl-1,2,3,4a,5,10b-hexahydro-4H-[1]-benzopyrano[3,4-b]pyridine.

EXAMPLE 14

A solution of 1.5 g of trans-4-benzyl-9-methoxy-1,2,3,4a,5,10b-hexahydro-4H-[1]-benzopyrano[3,4-b]pyridine in 30 ml of ethanol is hydrogenated at 300 kPa pressure in the presence of 0.5 g of 10% palladium on charcoal until one mole of hydrogen is consumed. The reaction mixture is filtered, evaporated to dryness to give 9-methoxy-1,2,3,4a,5,10b-hexahydro-4H-[1]-benzopyrano[3,4-b]pyridine.

EXAMPLE 15

To a suspension of 3.8 g of lithium aluminium hydride in 100 ml of tetrahydrofuran, 3.6 g of concentrated sulfuric acid is added dropwise at −5° to −10°, then 5.0 g of 9-methoxy-4-propionyl-1,2,3,4a,5,10b-hexahydro-4H-[1]-benzopyrano[3,4-b]pyridine is added slowly with stirring. The reaction mixture is allowed to warm to room temperature, stirred for 18 hours and finally heated under reflux for 1 hour. After cooling the reaction mixture is quenched with ethyl acetate, then treated with a small volume of water and 3N sodium hydroxide, filtered and concentrated in vacuo. The residue is redissolved in ethyl acetate and the ethyl acetate solution is washed with water, dried and evaporated to yield 9-methoxy-4-propyl-1,2,3,4a,5,10b-hexahydro-4H-[1]-benzopyrano[3,4-b]pyridine. The starting material is prepared by treatment of 9-methoxy-1,2,3,4a,5,10b-hexahydro-4H-[1]-benzopyrano[3,4-b]pyridine in the presence of two mole equivalents of powdered potassium carbonate in methylene chloride solution with 1 mole of propionyl chloride at room temperature overnight.

EXAMPLE 16

To a suspension of 20 g of 4-(3-aminopropyl)-6-methoxy-2H-[1]-benzopyran hydrochloride in 200 ml of ethyl acetate is added 12.5 g of bromine at room temperature. After 15 minutes at room temperature 24 g of triethylamine is added to yield 4-(3-aminopropylidene)-3-bromo-6-methoxy-2H-[1]-benzopyran and the reaction mixture is refluxed for 2 hours. After washing with water and drying the solvent is removed in vacuo. The residue is dissolved in ethanol and acidified with ethanolic hydrogen chloride to afford 9-methoxy-2,3,4a,5-tetrahydro-4H-[1]-benzopyrano[3,4-b]pyridine hydrochloride, m.p. 285°–286°.

The starting material is prepared as follows: To a solution of 26.9 g of 4-methoxyphenyl propargyl ether in 300 ml of tetrahydrofuran at $-70°$ is added 74 ml of 2.3M n-butyllithium in hexane. After 20 minutes at $-70°$, 26.2 g of 3-bromo-1-chloropropane in 86 ml of hexamethylphosphoramide is added and the reaction is stirred for 1 hour at 0°. After pouring onto water, the product is extracted with ether, and the solvent is removed in vacuo after drying over magnesium sulfate. Volatiles are removed at 150°/0.1 mmHg. The residue is dissolved in 400 ml of dimethylformamide, 45 g of potassium phthalimide is added and the reaction is heated at 50° for 16 hours. The reaction is poured onto water and the product is extracted with ether. After drying the solvent is removed in vacuo, and the residue is crystallized from isopropanol to afford 6-(4-methoxyphenoxy)-1-phthalimido-4-hexynylamine, m.p. 51°–53°.

A mixture of 40 g of 6-(4-methoxyphenoxy)-1-phthalimido-4-hexynylamine and 8.5 g of N,N-diethylaniline in 400 ml of N-methylpyrrolidinone is heated at 210° for 30 hours. After pouring onto water containing 57 ml of 1N hydrochloric acid the product is extracted with ether, dried, and the solvent is removed in vacuo. The residue is crystallized from isopropanol to afford 4-(3-phthalimidopropyl)-6-methoxy-2H-[1]-benzopyran, m.p. 78°–80°.

A mixture of 30 g of 4-(3-phthalimidopropyl)-6-methoxy-2H-[1]-benzopyran and 9 g of hydrazine hydrate in 600 ml of ethanol is refluxed for 2 hours. After removal of most of the solvent in vacuo, 10% sodium hydroxide is added and the product is extracted with ethyl acetate. After drying, the ethyl acetate solution is acidified with hydrochloric acid to give 4-(3-aminopropyl)-6-methoxy-2H-[1]-benzopyran hydrochloride, m.p. 141–142.

EXAMPLE 17

A mixture of 14 g of 9-methoxy-2,3,4a,5-tetrahydro-4H-[1]-benzopyrano[3,4-b]pyridine hydrochloride, 140 ml of ethanol, and a solution of 2.95 g of sodium carbonate in 10 ml of water and 3 g of 10% palladium on carbon catalyst is hydrogenated at 3 atm. pressure and 50° for 16 hours. After the addition of 15 g of propionaldehyde the hydrogenation is continued for an additional 16 hours under the same conditions. After filtration, the solvent is removed in vacuo. The residue is dissolved in ethanol and acidified with ethanolic hydrogen chloride to afford trans-9-methoxy-4-propyl-1,2,3,4a,5,10b-hexahydro-4H-[1]-benzopyrano[3,4-b]pyridine hydrochloride, m.p. 252°–254° (the compound of Example 2a).

EXAMPLE 18

(a) A solution of 400 mg of trans-7-allyloxy-4-methyl-1,2,3,4a,5,10b-hexahydro-4H-[1]-benzopyrano[3,4-b]pyridine hydrochloride in 10 ml of 1-methyl-2-pyrrolidinone is heated for 2 hours at 190°, poured onto water and the products extracted with ethyl acetate. After drying over magnesium sulfate, the solvent is removed; the residue is 20 ml of ethanol is hydrogenated at 3 atm. pressure in the presence of 100 mg of 10% palladium on carbon catalyst for 3 hours. After filtration, the solvent is removed and the hydrochloride salt is prepared with ethanolic hydrogen chloride to afford trans-7-hydroxy-4-methyl-10-propyl-1,2,3,4a,5,10b-hexahydro-4H-[1]-benzopyrano[3,4-b]pyridine hydrochloride, m.p. 283°–285°.

(b) The mother liquor is evaporated to dryness, the residue is converted to the free base and chromatographed on silica gel with acetone/hexane (1:3) as the eluent to yield trans-7-hydroxy-4-methyl-8-propyl-1,2,3,4a,5,10b-hexahydro-4H-[1]-benzopyrano[3,4-b]pyridine.

EXAMPLE 19

A solution of 628 mg of trans-7-methoxy-4-methyl-1,2,3,4a,5,10b-hexahydro-4H-[1]-benzopyrano[3,4-b]pyridine and 1 g of phenyl chloroformate in 20 ml of toluene is refluxed for 3 hours. After dilution with ether and washing with aqueous hydrochloric acid, the solvent is removed and 1 g of potassium hydroxide and 20 ml of dioxane is added. After refluxing for 2 hours, the reaction is diluted with water and the product extracted with ether. After drying and removal of solvent, the hydrochloride salt is prepared from ethanolic hydrogen chloride to afford trans-7-methoxy-1,2,3,4a,5,10b-hexahydro-4H-[1]-benzopyrano[3,4-b]pyridine hydrochloride, m.p. 207°–210°.

EXAMPLE 20

(a) A solution of 600 mg of trans-8-bromo-7-methoxy-4-propyl-1,2,3,4a,5,10b-hexahydro-4H-[1]-benzopyrano[3,4-b]pyridine in 10 ml of tetrahydrofuran is treated with 1.68 ml of 2.1M n-butyllithium at $-78°$. After 10 minutes, 27 ml of dimethylformamide is added. After 30 minutes at 0°, the reaction mixture is poured onto water and the products are extracted with ether. After drying the solvent is removed. The residue is treated with 35 mg of sodium borohydride in 5 ml of methanol. After 10 minutes the solvent is removed and the residue is chromatographed on 10 g silica gel with acetone/hexane 1:2 as the eluent to afford trans-8-hydroxymethyl-7-methoxy-4-propyl-1,2,3,4a,5,10b-hexahydro-4H-[1]-benzopyrano[3,4-b]pyridine.

(b) Reaction of trans-8-hydroxymethyl-7-methoxy-4-propyl-1,2,3,4a,5,10b-hexahydro-4H-[1]-benzopyrano[3,4-b]pyridine with diphenylphosphine and butyllithium according to the procedure of Example 9 and subsequent treatment with fumaric acid affords trans-7-hydroxy-8-hydroxymethyl-4-propyl-1,2,3,4a,5,10b-hexahydro-4H-[1]-benzopyrano[3,4-b]pyridine fumarate, m.p. 198°–200°.

EXAMPLE 21

A solution of 1.0 g of trans-8-bromo-7-hydroxy-4-methyl-1,2,3,4a,5,10b-hexahydro-4H-[1]-benzopyrano[3,4-b]pyridine in 10 ml of tetrahydrofuran is added to 160 mg of 50% sodium hydride in 10 ml of tetrahydrofuran and 10 ml of dimethylformamide. After 10 minutes at room temperature 420 mg of dimethyl sulfate is added and the reaction mixture is stirred for ½ hour. The reaction mixture is diluted with water and extracted with ether. After drying over magnesium sulfate the solvent is removed in vacuo, the residue dissolved in ethanolic hydrogen chloride and ether is added to afford trans-8-bromo-7-methoxy-4-methyl-1,2,3,4a,5,10b-hexahydro-4H-[1]-benzopyrano[3,4-b]pyridine hydrochloride, m.p. 265°–268°.

EXAMPLE 22

The following additional compounds are prepared by methods analogous to those described in the previous examples:

(a) 7-methoxy-2,4-dimethyl-2,3,4a,5-tetrahydro-4H-[1]-benzopyrano[3,4-b]pyridine hydrochloride, m.p. 236°–239°;

(b) trans-7-methoxy-4-methyl-10-propyl-1,2,3,4a,5,10b-hexahydro-4H-[1]-benzopyrano[3,4-b]pyridine hydrochloride, m.p. 173°–175°;

(c) trans-7-hydroxy-1,2,3,4a,5,10b-hexahydro-4H-[1]-benzopyrano[3,4-b]pyridine hydrochloride, m.p. 325° (dec.);

(d) trans-7-methoxy-4-methyl-8-propyl-1,2,3,4a,5,10b-hexahydro-4H-[1]-benzopyrano[3,4-b]pyridine hydrochloride, m.p. 181°–183°;

(e) trans-2-ethyl-9-methoxy-4-propyl-2,3,4a,5-tetrahydro-4H-[1]-benzo-pyrano[3,4-b]pyridine hydrochloride, m.p. 210°–212°;

(f) cis-2-ethyl-9-methoxy-4-propyl-2,3,4a,5-tetrahydro-4H-[1]-benzopyrano[3,4-b]pyridine hydrochloride, m.p. 206°–207°;

(g) 4-propyl-2,3,4a,5-tetrahydro-4H-[1]-benzopyrano[3,4-b]pyridine hydrochloride, m.p. 257°–259°;

(h) 4-butyl-2,3,4a,5-tetrahydro-4H-[1]-benzopyrano[3,4-b]pyridine hydrochloride, m.p. 241°–243°;

(i) trans-4-butyl-1,2,3,4a,5,10b-hexahydro-4H-[1]-benzopyrano[3,4-b]pyridine hydrochloride, m.p. 259°–262°;

(j) cis-4-butyl-1,2,3,4a,5,10b-hexahydro-4H-[1]-benzopyrano[3,4-b]pyridine hydrochloride, m.p. 186°–189°;

(k) trans-4-propyl-1,2,3,4a,5,10b-hexahydro-4H-[1]-benzopyrano[3,4-b]pyridine hydrochloride, m.p. 257°–262°;

(l) trans-10b-ethyl-9-hydroxy-4-propyl-1,2,3,4a,5,10b-hexahydro-4H-[1]-benzopyrano[3,4-b]pyridine hydrochloride, m.p. 242°–244°;

(m) trans-2$\beta$-ethyl-9-methoxy-4-propyl-1,2,3,4a,5,10b-hexahydro-4H-[1]-benzopyrano[3,4-b]pyridine hydrochloride, m.p. 194°–196°;

(n) 10-methoxy-4,8-dimethyl-2,3,4a,5-tetrahydro-4H-[1]-benzopyrano[3,4-b]pyridine hydrochloride, m.p. 244°–245°;

(o) 8-methoxy-4,10-dimethyl-2,3,4a,5-tetrahydro-4H-[1]-benzopyrano[3,4-b]pyridine hydrochloride, m.p. 235°–238°;

(p) trans-10-methoxy-4,8-dimethyl-1,2,3,4a,5,10b-hexahydro-4H-[1]-benzopyrano[3,4-b]pyridine hydrochloride, m.p. 228°–232°;

(q) 10-methoxy-4-methyl-2,3,4a,5-tetrahydro-4H-[1]-benzopyrano[3,4-b]pyridine hydrochloride, m.p. 247°–250°;

(r) trans-10-hydroxy-4-methyl-1,2,3,4a,5,10b-hexahydro-4H-[1]-benzopyrano[3,4-b]pyridine hydrochloride, m.p. 302°–305°;

(s) trans-10-benzyloxy-4-methyl-1,2,3,4a,5,10b-hexahydro-4H-[1]-benzopyrano[3,4-b]pyridine hydrochloride, m.p. 218°–220°;

(t) trans-10-methoxy-4-propyl-1,2,3,4a,5,10b-hexahydro-4H-[1]-benzopyrano[3,4-b]pyridine hydrochloride, m.p. 252°–255° (dec);

(u) trans-10-methoxy-4-methyl-1,2,3,4a,5,10b-hexahydro-4H-[1]-benzopyrano[3,4-b]pyridine hydrochloride, m.p. 231°–234°;

(v) trans-10-hydroxy-4-propyl-1,2,3,4a,5,10b-hexahydro-4H-[1]-benzopyrano[3,4-b]pyridine hydrochloride, m.p. 295°–297°;

(w) trans-7-methoxy-4-propyl-1,2,3,4a,5,10b-hexahydro-4H-[1]-benzopyrano[3,4-b]pyridine hydrochloride, m.p. 249°–251°;

(x) trans-8-hydroxy-4-propyl-1,2,3,4a,5,10b-hexahydro-4H-[1]-benzopyrano[3,4-b]pyridine hydrochloride, m.p. 275°–278° (dec.).

EXAMPLE 23

A mixture of 3 g of 9-methoxy-4-propyl-1,2,3,5-tetrahydro-4H-[1]-benzopyrano[3,4-b]pyridin-3-one in 100 ml of tetrahydrofuran is refluxed for 3 hours with 1.0 g of lithium aluminium hydride. After quenching with water, filtration and removal of solvent, the residue is treated with 1 g sodium cyanoborohydride in 50 ml of ethanol and 2 ml of glacial acetic acid. After 4 hours at room temperature, the reaction mixture is added to aqueous sodium carbonate solution, the product is extracted with ether, and the solvent is removed. The residue is converted to the hydrochloride salt to give cis and trans 9-methoxy-4-propyl-1,2,3,4a,5,10b-hexahydro-4H-[1]-benzopyrano[3,4-b]pyridine hydrochloride of Example 2.

The starting material is prepared as follows: A solution of 17.8 g of 6-methoxy-3-chromanone, 7.5 g of pyrrolidine and 0.1 ml of trifluoroacetic acid in 200 ml of toluene is refluxed for 8 hours in a Dean Stark apparatus. After removal of solvent in vacuo 14.0 g of acrylamide is added and the mixture is heated for 3 hours at 80°. Water is added, the organic layer is separated and evaporated to dryness to afford 9-methoxy-1,2,3,5-tetrahydro-4H-[1]-benzopyrano[3,4-b]pyridin-3-one.

A mixture of 2.31 g of the above compound is refluxed for 1 hour in tetrahydrofuran with 240 mg of sodium hydride; 2.0 g of propyl iodide is added and refluxing is continued for 2 hours. Aqueous workup and extraction gives 9-methoxy-4-propyl-1,2,3,5-tetrahydro-4H-[1]-benzopyrano[3,4-b]pyridin-3-one.

EAMPLE 24

9-Methoxy-4-propyl-2,3,4a,5-tetrahydro-4H-[1]-benzopyrano[3,4-b]pyridin-2-one is heated with lithium aluminium hydride in ether. The resulting product is hydrogenated in ethanol in the presence of 10% palladium on carbon catalyst to give 9-methoxy-4-propyl-1,2,3,4a,5,10b-hexahydro-4H-[1]-benzopyrano[3,4-b]pyridine.

The starting material is prepared as follows: A mixture of 2.57 g of 3-bromo-6-methoxy-4-chromanone and 3.3 g of the ethylene ketal of 1-(propylamino)-2-propanone in 500 ml of toluene is refluxed for 17 hours. The resulting product is dissolved in 20 ml of nitromethane and added to 50 ml of 85% polyphosphoric acid. After 48 hours at room temperature the reaction is poured onto ice to afford 9-methoxy-4-propyl-2,3,4a,5-tetrahydro-4H-[1]-benzopyrano[3,4-b]pyridin-2-one.

EXAMPLE 25

A mixture of 2.0 g of N-(3-chloropropyl)-propylamine and 1.78 g of 6-methoxy-3-chromanone in 100 ml of toluene is heated under reflux with water removal in a Dean Stark apparatus for 17 hours to yield after removal of the solvent 9-methoxy-4-propyl-1,2,3,5-tetrahydro-4H-[1]-benzopyrano[3,4-b]pyridine. Reduction with sodium cyanoborohydride in ethanol in the presence of glacial acetic acid gives 9-methoxy-4-propyl-1,2,3,4a,5,10b-hexahydro-4H-[1]-benzopyrano[3,4-b]pyridine of Example 2.

EXAMPLE 26

To a solution of 2.3 g of trans-8-bromo-7-methoxy-4-methyl-1,2,3,4a,5,10b-hexahydro-4H-[1]-benzopyrano[3,4-b]pyridine (Example 21) in 45 ml of tetrahydrofuran at −70° is added 5.6 ml of 2.6M t-butyllithium in hexane. After 5 minutes at −70°, 1.36 g of methyl iodide is added. After warming to 0°, the reaction mixture is diluted with ethyl acetate and washed with water. After drying over magnesium sulfate the solvent is removed in vacuo. Acidification of the residue with ethanolic hydrochloric acid yields trans-7-methoxy-4,8-dimethyl-1,2,3,4a,5,10b-hexahydro-4H-[1]-benzopyrano[3,4-b]pyridine hydrochloride, m.p. 277°-278°.

EXAMPLE 27

(a) A mixture of 21.6 l of 47–49% hydrobromic acid and 2.27 kg of trans-9-methoxy-4-propyl-1,2,3,4a,5,10b-hexahydro-4H-[1]-benzopyrano[3,4-b]pyridine hydrochloride is stirred and heated at 105°-110° for 2 hours. Most of the hydrobromic acid is then removed by distillation (125°/3 mmHg), a solution of 10.5 l of methanol and 9.5 l of water is added and the suspension heated to 75°. The hot mixture is cautiously treated with 2.2 l of 4N sodium hydroxide solution to pH 8, cooled to 10° and filtered. The collected solids are washed five times with 1 l of water each and dried (68°/3 mmHg) to yield trans-9-hydroxy-4-propyl-1,2,3,4a,5,10b-hexahydro-4H-[1]-benzopyrano[3,4-b]pyridine, m.p. 194°-196°.

(b) 1.71 kg of the above free base is dissolved in absolute ethanol at 78° and 0.3 kg of charcoal is added to the stirred solution. The mixture is filtered hot, the clear filtrate treated at 65°-70° with 630 ml of 12N hydrochloric acid, cooled to 10° and filtered to remove crystalline product. This material is washed two times with 500 ml of absolute ethanol each and dried (70°/0.2 mmHg to give trans-9-hydroxy-4-propyl-1,2,3,4a,5,10b-hexahydro-4H-[1]-benzopyrano[3,4-b]pyridine hydrochloride of Example 5a, m.p. 295°-297.5° (dec).

EXAMPLE 28

3.02 kg of bromine is added during 35 minutes to a mixture of 4.83 kg of 4-(3-aminopropyl)-8-methoxy-2H-[1]-benzopyran hydrochloride and 58 l of dichloromethane at 16°-23°, and once addition is complete the reaction is stirred for 3.5 hours at room temperature. 5.8 kg of triethylamine is added to yield 4-(3-aminopropylidene)-3-bromo-8-methoxy-2H-[1]-benzopyran.

The reaction is heated at 60° for 4 hours and then stirred overnight at room temperature. The mixture is washed five times with 12 l water each and 8 l of brine, dried with anhydrous sodium sulfate, filtered and the filtrate is evaporated at reduced pressure to give an oil. This is dissolved in 12 l of isopropanol, treated with 400 g of charcoal, and the mixture is filtered. The filtrate is cooled at 10°, treated with 1.8 l of 10N ethanolic hydrogen chloride and stirred for 1 hour at 5°-10°. The suspension is filtered; the product is washed three times with 4 l isopropanol each and dried 72 hours at 40°/400 Pa to give 7-methoxy-2,3,4a,5-tetrahydro-4H-[1]-benzopyrano[3,4-b]pyridine hydrochloride, m.p. 195°-198° (dec).

The starting material is prepared according to reaction sequence of Example 16 using 2-methoxyphenyl propargyl ether instead of 4-methoxyphenyl propargyl ether for the first reaction.

EXAMPLE 29

(a) A stirred mixture of 4.2 kg of 7-methoxy-2,3,4a,5-tetrahydro-4H-[1]-benzopyrano[3,4]pyridine hydrochloride, 900 g of anhydrous sodium carbonate, 42 l of ethanol, 3.02 l of water and 840 g of 10% palladium on carbon (50% water wet) is hydrogenated at 50° and 3 atm. pressure for 10 hours. The reaction is cooled and vented, 4 kg of propionaldehyde is added and the hydrogenation is continued at 50° for 24 hours. The reaction mixture is cooled and vented, adjusted to pH 12 with 1 l of 10N sodium hydroxide and filtered to remove catalyst. The filter is washed with 10 l of ethanol and 12 l of water, and the combined filtrates are evaporated at reduced pressure to give an oil. This is dissolved in 18 l of ethyl acetate and the solution is washed five times with 4 l of water each and 4 l of brine, dried over 10 kg of anhydrous sodium sulfate, filtered and evaporated at reduced pressure to give crude trans-7-methoxy-4-propyl-1,2,3,4a,5,10b-hexahydro-4H-[1]-benzopyrano[3,4-b]pyridine containing some cis isomer. The crude free base is dissolved in 12 l of absolute ethanol at 5° and 1.15 l of 12N ethanolic hydrogen chloride is added. The suspension is stirred for 15 minutes and filtered. The product is recrystallized from absolute ethanol and dried 24 hours (50°/13 Pa) to give pure trans-7-methoxy-4-propyl-1,2,3,4a,5,10b-hexahydro-4H-[1]-benzopyrano[3,4-b]pyridine hydrochloride, m.p. 250°-251° (dec).

(b) A mixture of 16.3 l of 47–49% hydrobromic acid and 1.63 kg of trans-7-methoxy-4-propyl-1,2,3,4a,5,10b-hexahydro-4H-[1]-benzopyranzo[3,4-b]pyridine hydrochloride is heated at 115°-120° for 5 hours. It is then added to 16 kg of ice and treated to pH 12 with a solution of 6.75 kg of sodium hydroxide in 11 l of water while maintaining the temperature below 30°. The mixture is adjusted to pH 9 with 800 ml of 37% hydrochloric acid and extracted four times with 12 l of ethyl acetate each. The combined extract is washed with 8 l of brine, dried with 5 kg of anhydrous sodium sulfate, treated with 230 g of charcoal, stirred for 30 minutes and filtered. The filtrate is evaporated at reduced pressure to give trans-7-hydroxy-4-propyl-1,2,3,4a,5,10b-hexahydro-4H-[1]-benzopyrano[3,4-b]pyridine, m.p. 111°-114°.

(c) A mixture of 1.3 kg of trans-7-hydroxy-4-propyl-1,2,3,4a,5,10b-hexahydro-4H-[1]-benzopyrano[3,4-b]pyridine and 7.8 l of absolute ethanol is heated at 60° until a solution is obtained. It is then filtered and the filtrate is treated with 525 ml of 37% hydrochloric acid and the mixture is stirred overnight at room temperature. The suspension is cooled to 0°–5° and filtered; the solid is washed four times with 250 ml of absolute ethanol each and dried 4 hours (80°/3 mmHg) to yield trans-7-hydroxy-4-propyl-1,2,3,4a,5,10b-hexahydro-4H-[1]-benzopyrano[3,4-b]pyridine hydrochloride of example 7c, m.p. 264°–265.5° (dec).

EXAMPLE 30

The following additional compounds are prepared by procedures analogous to those described in the previous examples:
(a) 10-methoxy-4-propyl-2,3,4a,5-tetrahydro-4H-[1]-benzopyrano[3,4-b]pyridine hydrochloride, m.p. 252°–254°,
(b) trans-8-ethyl-7-methoxy-4-methyl-1,2,3,4a,5,10b-hexahydro-4H-[1]-benzopyrano[3,4-b]pyridine hydrochloride, m.p. 217°–221°,
(c) trans-7-ethoxy-4,8-dimethyl-1,2,3,4a,5,10b-hexahydro-4H-[1]-benzopyrano[3,4-b]pyridine hydrochloride, m.p. 248°–251°,
(d) trans-10-methoxy-8-methyl-4-propyl-1,2,3,4a,5,10b-hexahydro-4H-[1]-benzopyrano[3,4-b]pyridine hydrochloride, m.p. 251°–253°,
(e) trans-10-benzyloxy-8-methyl-4-propyl-1,2,3,4a,5,10b-hexahydro-4H-[1]-benzopyrano[3,4-b]pyridine hydrochloride, m.p. 214°–215°,
(f) trans-10-hydroxy-8-methyl-4-propyl-1,2,3,4a,5,10b-hexahydro-4H-[1]-benzopyrano[3,4-b]pyridine hydrochloride, m.p. 287°–291°,
(g) trans-8-bromo-7-methoxy-4-propyl-1,2,3,4a,5,10b-hexahydro-4H-[1]-benzopyrano[3,4-b]pyridine hydrochloride, m.p. 210°–211°,
(h) trans-8-ethyl-10-methoxy-4-propyl-1,2,3,4a,5,10b-hexahydro-4H-[1]-benzopyrano[3,4-b]pyridine hydrochloride, m.p. 231°–233°,
(i) trans-7-bromo-10-methoxy-4-propyl-1,2,3,4a,5,10b-hexahydro-4H-[1]-benzopyrano[3,4-b]pyridine hydrochloride, m.p. 267°–270°,
(j) trans-10-ethoxy-4-propyl-1,2,3,4a,5,10b-hexahydro-4H-[1]-benzopyrano[3,4-b]pyridine hydrochloride, m.p. 247°–250°,
(k) trans-10-benzyloxy-4-propyl-1,2,3,4a,5,10b-hexahydro-4H-[1]-benzopyrano[3,4-b]pyridine hydrochloride, m.p. 184°–185°,
(l) trans-10-benzyloxy-7-bromo-4-propyl-1,2,3,4a,5,10b-hexahydro-4H-[1]-benzopyrano[3,4-b]pyridine hydrochloride, m.p. 210°–212°,
(m) trans-7-methoxy-8-methyl-4-propyl-1,2,3,4a,5,10b-hexahydro-4H-[1]-benzopyrano[3,4-b]pyridine hydrochloride, m.p. 243°–246°,
(n) trans-7-hydroxy-4,8-dimethyl-1,2,3,4a,5,10b-hexahydro-4H-[1]-benzopyrano[3,4-b]pyridine hydrochloride, m.p. 252°–254°.

EXAMPLE 31

To a solution of 2.61 g of cis-9-methoxy-4-propyl-1,2,3,4a,5,10b-hexahydro-4H-[1]-benzopyrano[3,4-b]pyridine in 30 ml of dry dimethyl sulfoxide is added 2.0 g of potassium-t-butoxide. After 2 days at room temperature the reaction mixture is poured onto water and the product is extracted with ether. After drying over magnesium sulfate the solvent is removed in vacuo to afford a 1:1 mixture of the cis and trans isomers. Acidification with ethanolic hydrochloric acid affords trans-9-methoxy-4-propyl-1,2,3,4a,5,10b-hexahydro-4H-[1]-benzopyrano[3,4-b]pyridine hydrochloride, melting at 252°–254°.

EXAMPLE 32

A mixture of 2.19 g of trans-7-methoxy-1,2,3,4a,5,10b-hexahydro-4H-[1]-benzopyrano[3,4-b]pyridine, 0.80 g of allyl chloride, 2.0 g of calcium carbonate in 20 ml of dry dimethylformamide is heated at 80° for 16 hours. After dilution with water the product is extracted with ether. After drying over magnesium sulfate the solvent is removed in vacuo. Acidification with ethanolic hydrochloric acid affords trans-4-allyl-7-methoxy-1,2,3,4a,5,10b-hexahydro-4H-[1]-benzopyrano[3,4-b]pyridine hydrochloride. Hydrogenation of said compound in the presence of 500 mg of 10% palladium on carbon catalyst at 3 atm. pressure for 6 hours at room temperature in water affords trans-7-methoxy-4-propyl-1,2,3,4a,5,10b-hexahydro-4H-[1]-benzopyrano[3,4-b]pyridine hydrochloride.

EXAMPLE 33

Preparation of 1,000 capsules each containing 10 mg of the active ingredient of example 5a with the formula as follows:
trans-9-Hydroxy-4-propyl-1,2,3,4a,5,10b-hexahydro-4H-[1]-benzopyrano[3,4-b]pyridine hydrochloride: 10.0 g
Lactose: 207.0 g
Modified starch: 80.0 g
Magnesium stearate: 3.0 g Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing 10–200 mg of the other compounds disclosed and exemplified herein.

EXAMPLE 34

Preparation of 10,000 tables each containing 10 mg of the active ingredient of example 7c with the formula as follows:
trans-7-Hydroxy-4-propyl-1,2,3,4a,5,10b-hexahydro-4H-[1]-benzopyrano[3,4-b]pyridine hydrochloride: 100.0 g
Lactose: 2,535.0 g
Corn starch: 125.0 g
Polyethylene glycol 6,000: 150.0 g
Magnesium stearate: 40.0 g
Purified water: q.s.

Procedure: All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, wich are granulated, if necessary, with an additional amount of water. The granulate is dried overnight at 35°, broken on a screen with 1.2 mm openings and compressed into tablets, using concave punches uppers bisected.

Analogously tablets are prepared, containing 10–200 mg of one of the other compounds disclosed and exemplified herein.

What is claimed is:
1. A compound of the formula

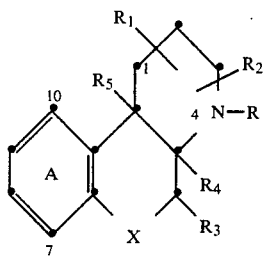

wherein X represents oxygen or sulfur; ring A is unsubstituted or substituted by one to three identical or different substituents selected from hydroxy, hydroxy-lower alkyl, etherified hydroxy, etherified hydroxy-lower alkyl, acyloxy, acyloxy-lower alkyl, halogen, lower alkyl, trifluoromethyl, amino, mono- and di-lower alkylamino and acylamino; or ring A is substituted by one lower alkylenedioxy; R represents hydrogen, lower alkyl or aryl-lower alkyl; $R_1$ represents hydrogen, lower alkyl, lower alkylthio-lower alkyl, amino, acylamino, (amino, mono- or di-lower alkylamino)-lower alkyl, carboxy, lower alkoxycarbonyl, carbamoyl or mono- or di-lower alkylcarbamoyl; $R_2$ to $R_5$ represent hydrogen or lower alkyl; and wherein within the definitions the term acyl represents lower alkanoyl, aroyl, lower alkoxycarbonyl, carbamoyl or mono- or di-lower alkylcarbamoyl; the term aryl represents phenyl or phenyl substituted by one to three of lower alkyl, lower alkoxy, halogen or trifluoromethyl; and aroyl represents benzoyl or benzenesulfonyl, benzoyl or benzenesulfonyl substituted by one to three of lower alkyl, lower alkoxy, halogen or trifluoromethyl, thienoyl, pyrroloyl, or 2-, 3- or 4-pyridylcarbonyl; a dehydro derivative thereof with a double bond at the 1,2-position, or at the 1,10b-position in which case $R_5$ is absent; or a pharmaceutically acceptable salt thereof.

2. A compound of claim 1 of the formula Ia or Ib

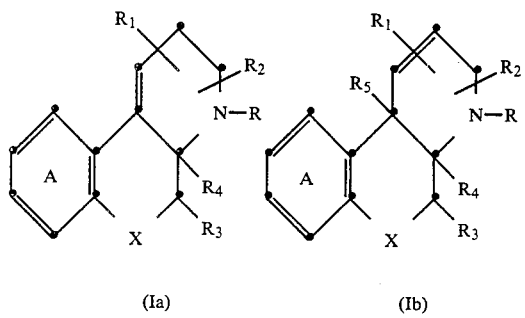

wherein ring A, R and $R_1$ to $R_5$ are as defined in said claim; or a pharmaceutically acceptable salt thereof.

3. A compound of claim 1 of the formula I, Ia or Ib, wherein X represents oxygen; or a pharmaceutically acceptable salt thereof.

4. A compound of claim 1 of the formula I, Ia or Ib, wherein X represents sulfur; or a pharmaceutically acceptable salt thereof.

5. A compound of claim 1 of formula I, formula Ia or formula Ib wherein X represents oxygen or sulfur; ring A is unsubstituted or substituted by one to three substituents selected from hydroxy, acyloxy, etherified hydroxy, hydroxymethyl, acyloxymethyl, etherified hydroxymethyl, lower alkyl, halogen and trifluoromethyl; or ring A is substituted by one lower alkylenedioxy; R, $R_1$ to $R_5$ represent hydrogen or lower alkyl; or a pharmaceutically acceptable salt thereof.

6. A compound of claim 5 wherein X represents oxygen; or a pharmaceutically acceptable salt thereof.

7. A compound of claim 1 of the formula

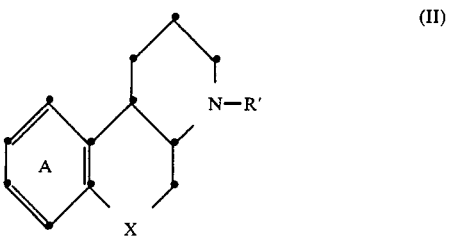

wherein ring A is unsubstituted or substituted by one to three identical or different substituents selected from hydroxy, hydroxymethyl, acyloxy, acyloxymethyl, lower alkyl, lower alkoxy and halogen; X represents oxygen or sulfur; R' represents lower alkyl; and wherein within the above definitions the term acyloxy represents lower alkanoyloxy, aroyloxy, heteroaroyloxy, lower alkoxycarbonyloxy, carbamoyloxy, or mono-or di-lower alkylcarbamoyloxy; aroyloxy represents benzoyloxy or benzoyloxy substituted on the benzene ring by one to three of lower alkyl, lower alkoxy, halogen or trifluoromethyl; heteroaroyloxy represents 2-, 3- or 4-pyridylcarbonyloxy; a 1,10b-dehydro derivative thereof; or a pharmaceutically acceptable salt thereof.

8. A compound of claim 7 of the formula II wherein X represents oxygen; ring A is monosubstituted by hydroxy, lower alkanoyloxy, benzoyloxy or pyridylcarbonyloxy; R' represents lower alkyl of 1 to 4 carbon atoms; or a pharmaceutically acceptable salt thereof.

9. A compound of claim 7 with a trans ring fusion; or a pharmaceutically acceptable salt thereof.

10. A compound of claim 7 of the formula II wherein X is oxygen or sulfur; R' is alkyl of 3 to 5 carbon atoms; ring A is monosubstituted at the 7-, 8- or 9-position by hydroxy, acyloxy, hydroxymethyl or acyloxymethyl; or ring A is disubstituted at two of the 7-, 8- or 9-positions by one of the groups chosen from hydroxy and acyloxy and the other group chosen from hydroxy, acyloxy and halogen; a 1,10b-dehydro derivative thereof; or a pharmaceutically acceptable salt thereof.

11. A compound of claim 7, as the trans ring-fused isomer thereof, wherein X is oxygen; R' is straight chain alkyl or 3 to 5 carbon atoms; ring A is monosubstituted at the 7-, 8- or 9-position by hydroxy, lower alkanoyloxy, aroyloxy, hydroxymethyl, lower alkanoyloxymethyl or aroyloxymethyl; or a pharmaceutically acceptable salt thereof.

12. A compound of claim 7, as the trans ring-fused isomer thereof, wherein x is oxygen; R' is methyl, ethyl or n-propyl; ring A is monosubstituted at the 7- or 10-position by hydroxy, lower alkoxy, lower alkanoyloxy, benzoyloxy or nicotinoyloxy; or ring A is disubstituted, at the 7- and 8-, 7 and 10, or 8- and 10-positions by one group chosen from hydroxy and lower alkoxy and the other group chosen from lower alkyl and halogen; or a pharmaceutically acceptable salt thereof.

13. A compound of claim 7, as the trans ring-fused isomer thereof wherein X is oxygen; ring A is monosubstituted at the 7- or 9-position by hydroxy, lower alkanoyloxy, benzoyloxy or nicotinoyloxy; R' is n-propyl or n-butyl; or a pharmaceutically acceptable salt thereof.

14. A compound of claim 1 of the formula III

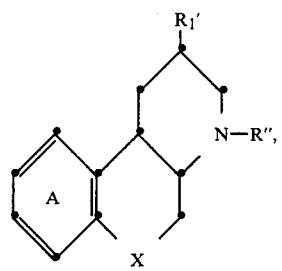

(III)

wherein ring A is unsubstituted or substituted by one to three identical or different substituents selected from hydroxy, hydroxymethyl, acyloxy, acyloxymethyl, lower alkoxy and halogen; X represents oxygen or sulfur; R'' represents lower alkyl; $R_1'$ represents lower alkylthio-lower alkyl, acylamino, (amino, mono- or di-lower alkylamino)-lower alkyl, carboxy, lower alkoxycarbonyl, carbamoyl, mono- or di-lower alkylcarbamoyl; or a pharmaceutically acceptable salt thereof.

15. A compound of claim 7 being trans-4-propyl-9-hydroxy-1,2,3,4a,5,10b-hexahydro-4H-[1]-benzopyrano[3,4-b]pyridine or a pharmaceutically acceptable salt thereof.

16. A compound of claim 7 being trans-4-propyl-7-hydroxy-1,2,3,4a,5,10b-hexahydro-4H-[1]-benzopyrano[3,4-b]pyridine or a pharmaceutically acceptable salt thereof.

17. A compound of claim 7 being trans-4-propyl-9-hydroxy-2,3,4a,5-tetrahydro-4H-[1]-benzothiopyrano[3,4-b]pyridine hydrochloride or a pharmaceutically acceptable salt thereof.

18. A compound of claim 12 wherein ring A is mono substituted at the 10-position by hydroxy or lower alkoxy; or ring A is disubstituted, at the 7-position by hydroxy or lower alkoxy and at the 8-position by lower alkyl or halogen; or a pharmaceutically acceptable salt thereof.

19. A compound of claim 18 being trans-10-hydroxy-4-propyl-1,2,3,4a,5,10b-hexahydro-4H-[1]-benzopyrano[3,4-b]-pyridine or a pharmaceutically acceptable salt thereof.

20. A compound of claim 18 being trans-10-methoxy-4-propyl-1,2,3,4a,5,10b-hexahydro-4H[1]-benzopyrano[3,4-b]pyridine or a pharmaceutically acceptable salt thereof.

21. A compound of claim 18 being trans-7-hydroxy-4,8-dimethyl-1,2,3,4a,5,10b-hexahydro-4H[1]benzopyrano[3,4-b]pyridine or a pharmaceutically acceptable salt thereof.

22. A process of preparing a compound of formula II having a trans-4a,10b-ring junction according to claim 9, which comprises treating a corresponding compound of formula II having a cis-4a,10b-ring junction with a strong base; and, if required, separating a said compound of formula II having a trans-4a,10b-ring junction from a mixture of isomers.

23. A presynaptic dopamine receptor stimulating or serotonin receptor stimulating pharmaceutical composition suitable for administration to a mammal comprising an effective presynaptic dopamine receptor stimulating or serotonin receptor stimulating amount of a compound of claim 1 in combination with one or more pharmaceutically acceptable carriers.

24. A method of treating psychotropic disorders responsive to the stimulation of presynaptic dopamine or of serotonin central nervous system receptors in mammals comprising the administration to a mammal in need thereof of an effective presynaptic dopamine receptor stimulating or serotonin receptor stimulating amount of a compound of claim 1 or of a presynaptic dopamine receptor stimulating or serotonin receptor stimulating pharmaceutical composition comprising a said compound in combination with one or more pharmaceutically acceptable carriers.

25. A method of stimulating serotonin or presynaptic dopamine receptors in mammals comprising the administration to a mammal in need thereof of an effective serotonin or presynaptic dopamine receptor stimulating amount of a compound of claim 1 or of a pharmaceutical composition comprising a said compound in combination with one or more pharmaceutically acceptable carriers.

26. A method of stimulating serotonin or presynaptic dopamine receptors in mammals comprising the administration to a mammal in need thereof of an effective serotonin or presynaptic dopamine receptor stimulating amount of a compound of claim 7 or of a pharmaceutical composition comprising a said compound of combination with one or more pharmaceutically acceptable carriers.

27. A method of stimulaing presynaptic dopamine receptors in mammals comprising the administration to a mammal in need thereof of an effective presynaptic dopamine receptor stimulating amount of a compound of claim 15, trans-4-propyl-9-hydroxy-1,2,3,4a,5,10b-hexahydro-4H-[1]-benzopyrano[3,4-b]pyridine or a pharmaceutically acceptable salt thereof, or of a pharmaceutical composition comprising a said compound in combination with one or more pharmaceutically acceptable carriers.

28. A method of stimulating presynaptic dopamine receptors in mammals comprising the administration to a mammal in need thereof of an effective presynaptic dopamine receptor stimulating amount of a compound of claim 16, trans-4-propyl-9-hydroxy-1,2,3,4a,5,10b-hexahydro-4H-[1]-benzopyrano[3,4-b]pyridine or a pharmaceutically acceptable salt thereof, or of a pharmaceutical composition comprising a said compound in combination with one or more pharmaceutically acceptable carriers.

* * * * *

UNITED STATES PATENT AND TRADEMARK OFFICE
CERTIFICATE OF CORRECTION

PATENT NO. : 4,604,397
DATED     : August 5, 1986
INVENTOR(S) : Alan J. Hutchison It is certified that error appears in the above—identified patent and that said Letters Patent is hereby corrected as shown below:

Column 16, lines 15-25, structure (XIX) should read --

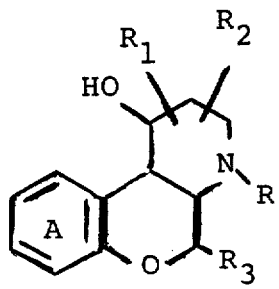

(XIX)

--.

Signed and Sealed this

Eleventh Day of October, 1988

*Attest:*

DONALD J. QUIGG

*Attesting Officer*          *Commissioner of Patents and Trademarks*

UNITED STATES PATENT AND TRADEMARK OFFICE
CERTIFICATE OF CORRECTION

PATENT NO. : 4,604,397  Page 1 of 5
DATED : AUGUST 5, 1986
INVENTOR(S) : ALAN J. HUTCHISON It is certified that error appears in the above-identified patent and that said Letters Patent is hereby corrected as shown below:

Column 8, line 2 should read -- trans 10-bromo-7-methoxy-4-methyl --.

Column 8, line 13 should read -- trans 10-bromo-7- --.

Column 8, line 19 should read --4,10-dimethyl-1,2,3,4a,5,10b-hexahydro-4H-[1]-ben- --.

Column 9, line 9 should read -- alkoxy and at the 10-position by lower alkyl or halogen.

UNITED STATES PATENT AND TRADEMARK OFFICE
CERTIFICATE OF CORRECTION

PATENT NO. : 4,604,397

DATED : AUGUST 5, 1986

INVENTOR(S) : ALAN J. HUTCHISON

It is certified that error appears in the above-identified patent and that said Letters Patent is hereby corrected as shown below:

Column 30, line 3, should read -- hydrogen chloride to afford trans-10-bromo-7 --.

Column 32, line 18 should read -- to afford trans-7-hydroxy-4-methyl-8-propyl- --.

Column 32, line 24, should read -- eluent to yield trans-7-hydroxy-4-methyl-10-propyl- --.

Column 32, line 45, should read -- A solution of 600 mg of trans-10-bromo-7-methoxy-4- --.

Column 32, line 58, should read -- afford trans-10-hydroxymethyl-7-methoxy-4-propyl- --.

UNITED STATES PATENT AND TRADEMARK OFFICE
CERTIFICATE OF CORRECTION

PATENT NO. : 4,604,397

DATED : AUGUST 5, 1986

INVENTOR(S) : ALAN J. HUTCHISON

It is certified that error appears in the above-identified patent and that said Letters Patent is hereby corrected as shown below:

Column 32, line 61, should read -- Reaction of trans-10-hydroxymethyl-7-methoxy-4- --.

Column 32, line 66, should read -- trans-7-hydroxy-10-hydroxymethyl-4-propyl- --.

Column 33, line 3, should read -- A solution of 1.0 g of trans-10-bromo-7-hydroxy-4- --.

Column 33, line 14, should read -- added to afford trans-10-bromo-7-methoxy-4-methyl- --.

Column 33, line 25 should read -- (b) trans-7-methoxy-4-methyl-8-propyl-1,2,3,4a,5,10b- --.

UNITED STATES PATENT AND TRADEMARK OFFICE
CERTIFICATE OF CORRECTION

PATENT NO. : 4,604,397

DATED : AUGUST 5, 1986

INVENTOR(S) : ALAN J. HUTCHISON

It is certified that error appears in the above-identified patent and that said Letters Patent is hereby corrected as shown below:

Column 33, line 31, should read -- (d) trans-7-methoxy-4-methyl-10-propyl-1,2,3,4a,5,10b- --.

Column 35, line 20, should read -- To a solution of 2.3 g of trans-10-bromo-7-methoxy-4- --.

Column 35, line 30 should read -- methoxy-4,10-dimethyl-1,2,3,4a,5,10b-hexahydro-4H- --.

Column 37, line 18, should read -- (b) trans-10-ethyl-7-methoxy-4-methyl-1,2,3,4a,5,10b- --.

Column 37, line 21, should read -- (c) trans-7-ethoxy-4,10-dimethyl-1,2,3,4a,5,10b-hexahy- --.

UNITED STATES PATENT AND TRADEMARK OFFICE
CERTIFICATE OF CORRECTION

PATENT NO. : 4,604,397

DATED : AUGUST 5, 1986

INVENTOR(S) : ALAN J. HUTCHISON

It is certified that error appears in the above-identified patent and that said Letters Patent is hereby corrected as shown below:

Column 37, line 33, should read -- (g) trans-10-bromo-7-methoxy-4-propyl-1,2,3,4a,5,10b- --.

Column 37, line 51, should read -- (m) trans-7-methoxy-10-methyl-4-propyl-1,2,3,4a,5,10b- --.

Column 37, line 54, should read -- (n) trans-7-hydroxy-4,10-dimethyl-1,2,3,4a,5,10b-hex- --.

Column 41, line 42, should read -- droxy or lower alkoxy and at the 10-position by lower --.

Column 41, line 53 should read -- 4,10-dimethyl-1,2,3,4a,5,10b-hexahydro-4H[1]ben- --.

Signed and Sealed this

Twenty-first Day of March, 1989

Attest:

DONALD J. QUIGG

Attesting Officer

Commissioner of Patents and Trademarks